US007785890B2

(12) United States Patent
Reboud et al.

(10) Patent No.: US 7,785,890 B2
(45) Date of Patent: Aug. 31, 2010

(54) METHOD AND DEVICE FOR THE ANALYSIS OF LIVING REACTION MEDIA

(75) Inventors: Julien Reboud, Grenoble (FR); Béatrice Schaack, Grenoble (FR); François Chatelain, Voreppe (FR)

(73) Assignee: Commissariat A L'Energie Atomique, Paris (FR)

( * ) Notice: Subject to any disclaimer, the term of this patent is extended or adjusted under 35 U.S.C. 154(b) by 1065 days.

(21) Appl. No.: 10/563,817

(22) PCT Filed: Jul. 9, 2004

(86) PCT No.: PCT/FR2004/001810

§ 371 (c)(1),
(2), (4) Date: Jun. 29, 2006

(87) PCT Pub. No.: WO2005/008238

PCT Pub. Date: Jan. 27, 2005

(65) Prior Publication Data
US 2007/0065946 A1  Mar. 22, 2007

(30) Foreign Application Priority Data
Jul. 11, 2003  (FR) .................................. 03 08526

(51) Int. Cl.
*G01N 33/48* (2006.01)
*G01N 24/00* (2006.01)
*C12Q 1/02* (2006.01)

(52) U.S. Cl. .................. 436/63; 436/46; 436/173; 436/174; 435/4; 435/29; 435/283.1; 435/287.1; 435/287.9; 435/288.3; 435/288.4; 422/68.1; 250/281; 250/282; 250/288

(58) Field of Classification Search ............... 436/43, 436/46, 63, 173, 174, 180, 181; 435/4, 29, 435/30, 283.1, 287.1, 287.9, 288.3, 288.4; 422/57, 68.1; 250/281, 282, 287, 288
See application file for complete search history.

(56) References Cited

U.S. PATENT DOCUMENTS

| 6,218,191 | B1 * | 4/2001 | Palander ..................... 436/63 |
| 6,265,715 | B1 * | 7/2001 | Perreault et al. ............. 250/288 |
| 6,632,656 | B1 * | 10/2003 | Thomas et al. ............. 435/288.5 |
| 7,456,392 | B2 * | 11/2008 | Engelking et al. ............ 250/288 |
| 2002/0051738 | A1 * | 5/2002 | Schurenberg et al. ......... 422/102 |
| 2002/0068133 | A1 * | 6/2002 | Jarrell et al. .................. 427/596 |
| 2002/0158196 | A1 | 10/2002 | Berggren et al. |
| 2003/0010908 | A1 * | 1/2003 | Clark et al. ................... 250/288 |
| 2003/0057368 | A1 * | 3/2003 | Franzen et al. ............... 250/281 |

FOREIGN PATENT DOCUMENTS

| EP | 1 284 495 | 2/2003 |
| WO | 01/26460 | 4/2001 |
| WO | 01/84143 | 11/2001 |
| WO | 2004/011938 | * 2/2004 |

* cited by examiner

*Primary Examiner*—Maureen M Wallenhorst
(74) *Attorney, Agent, or Firm*—Oblon, Spivak, McClelland, Maier & Neustadt, L.L.P.

(57) ABSTRACT

A method and device for analysis of reaction media containing one or more cells. This method and device can be used to perform an automated high-throughput analysis.

31 Claims, 12 Drawing Sheets

Figure 2: Transfection by fusion of drops: G1 + R

Figure 4: Fusion of cell drops G1+G2 after transfection

*Example of the expression of a recombinant protein in a suspension of glial cells and of the activation of a suspension of neurones*

Figure 5: Photocleavage device

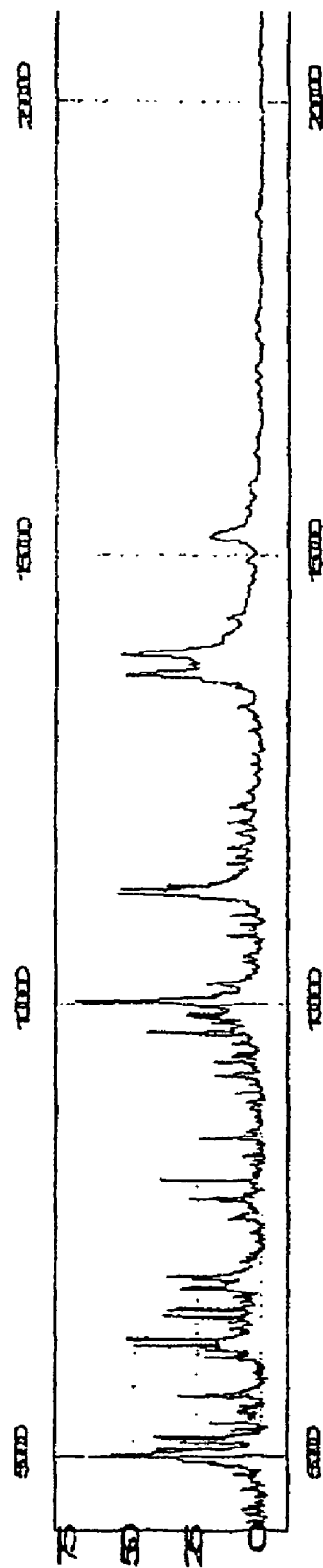
Figure 11: Example of a spectrum obtained without CDDP and without TNF. Along the x-axis is the mass to charge ratio in Daltons (Da); along the y-axis is the signal intensity (100 corresponds to the saturation of the detector).

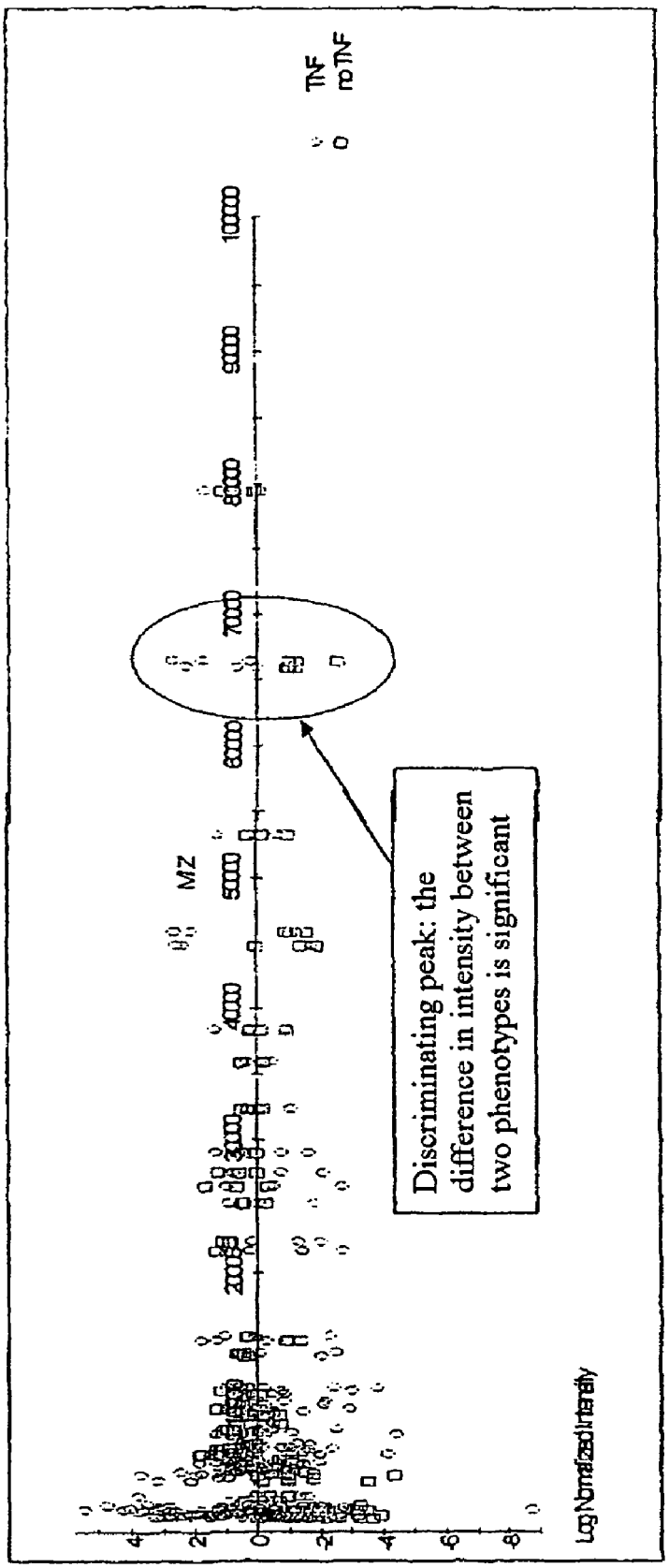
Figure 12: Representation of the differences between the spectra of the two phenotypes without TNF and with TNF

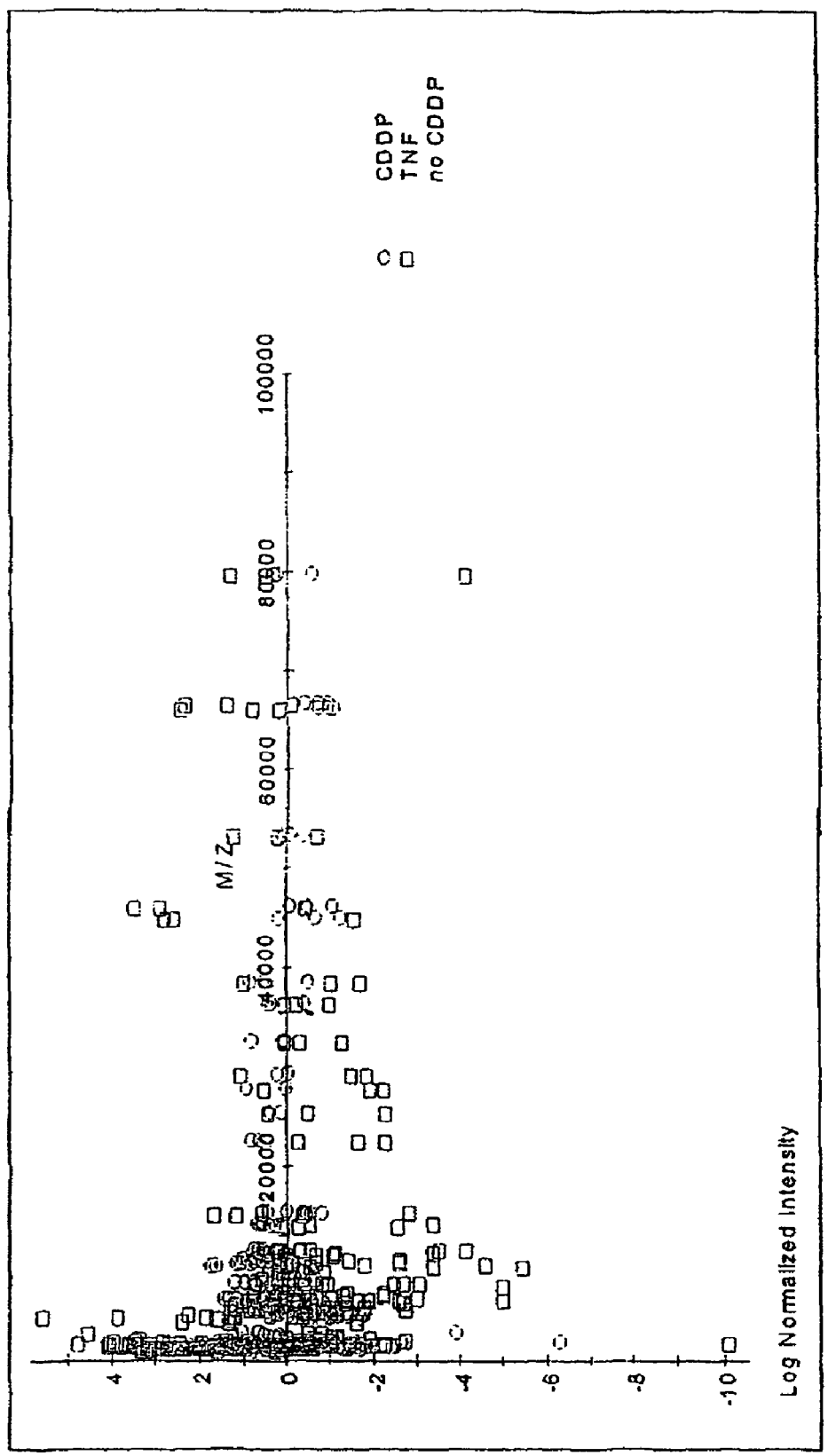
Figure 13: Representation of the differences between the spectra of the three phenotypes without TNF or CDDP, with TNF and with CDDP

METHOD AND DEVICE FOR THE ANALYSIS OF LIVING REACTION MEDIA

BACKGROUND OF THE INVENTION

1. Field of the Invention

The present invention relates to a method and a device for the analysis of reaction media comprising one or more cells, this method and this device making it possible to perform an automated high-throughput analysis.

2. Description of the Related Art

Currently, in biological research, and in particular in the pharmaceutical field, attempts have been made to analyze the phenotype of cell populations, and more particularly the proteome, in response to one or more stimulations exerted on these cell populations, so as to evaluate the impact of these stimulations on the cells to which they are applied. This analysis requires tools for carrying out reactions on living reaction media (cell populations) and the analysis of these reaction media under conditions such that there is no (or as little as possible) distortion of the reaction medium between these two steps, so as to limit the loss or transformation of the information.

There exists, in this research field, an increasing demand in terms of sample processing throughput. An increasing number of molecules are available to be tested, and increasingly varied cell systems (tissues, networks, cells) are available to be studied.

There exists therefore a need for tools for analyzing living reaction media, which make it possible to study these reaction media with as much objectivity as possible and with a processing rate that is as high as possible.

The present invention, which allies the culturing of cell populations on matrix supports and analysis by mass spectrometry, makes it possible to satisfy these expectations.

At the current time, phenotypic screening is carried out essentially using calorimetric methods, or fluorescent or radioactive molecules. These methods require the labeling of specific molecules, which means that the protein(s) investigated must be known beforehand. The present invention does not require any prior knowledge of the expected modifications of the cells subsequent to the stimuli.

Many methods today make it possible to analyze more or less directly the phenotype of one or more cells with a more or less rapid throughput.

The analyses directly using cells all have an operating principle in common, but differ with respect to the signal analyzed at output, which represents the phenotype:
optical signal: fluorescence, luminescence, colorimetry.
radioactive signal: labeled molecules.
electrical signal: electrophysiology.

These various analytical methods are generally implemented in a plastic well format (96 or 384 wells per plate) which also requires a large amount of reagents (0.1 to 0.5 ml per well in a 96-well plate) and allows only a moderate throughput.

In addition, the signal is not directly representative of the phenotype, but requires a calibration that is often complex.

It is, moreover, difficult to directly analyze cell secretions, except by means of antibody uptake methods.

Analysis of the various phenotypes is done only on the basis of a single parameter, a molecule that is known, and for which the intention is to verify whether it is present or not: it is necessary, at the start, to know which molecule is being sought. For example, when the intention is to study the presence of a molecule in the cell, it is necessary, at the start, to have quite a precise idea of the various properties of this molecule, so as to couple it to a specific antibody or render the molecule fluorescent. It is also possible to look for post-translational modifications of proteins, but by targeting a specific modification.

Research relating to the limit of the performance and processing rate of these various methods has led to the development of a format that is more suited to very high-throughput handling. The first example of the result of this research is DNA chips: the messenger RNAs expressed by a cell population (after stimulation) are screened in the form of deposits on a matrix support, or chip, containing DNA fragments potentially complementary to this expression. This method makes it possible to assess the level of expression of several thousand genes on a chip.

However, the results are often not demonstrative enough to be able to do without a finer study after a first analysis. In fact, this method involves sample processing steps (collection and multiplication of the amount of RNA, reverse PCR) that move away from the cellular model under consideration. In addition, it only makes it possible to analyze the level of expression of RNA, which is not directly related to the amount of proteins produced, nor to the qualities thereof, due in particular to post-translational modifications (alternative splicing, modified quaternary 3D conformation, phosphorylation, assembly).

Other molecule chips attempt to overcome this distancing by trying to directly analyze the level of expression of various molecules within the cell culture. Thus, various molecules have been deposited in the form of a matrix on supports in the chip format: RNA, proteins, sugars, for example. Unfortunately, the techniques used are not really reliable, and are intended to analyze interactions between molecules rather that a cell phenotype.

Finally, even though the number of different molecules analyzed on a chip is large, a choice has already been made with regard to the molecules that are deposited onto the support. This approach implies prior knowledge of the phenotypes being sought, which restricts the analytical possibilities.

As regards cell chips, they have been described by Sabatini et al. These cell chips function in the following way: DNA is deposited in the form of a dispersion in gelatin, as a matrix, on a glass slide. After drying, the positions comprising DNA are treated with a lipid based transfection agent and the plate is then placed in a medium into which cells are dispensed.

On the glass slide, the gelatinized DNA is present in solid form and the transfection takes place in a semi-solid phase, by binding the molecules adjacent to the DNA deposits to lipids that promote penetration of the DNA into the cells adjacent to the DNA deposits. A matrix of transfected cells at the positions corresponding to the DNA deposits is obtained. This method has the drawback of not being very precise and of being nonreproducible. The attachment by the gelatin does not make it possible to control the detachment of the transfected DNA. Neither does it make it possible to improve the transfection efficiency. Using this method, the expression or the blocking of the expression of a sufficient amount of protein is difficult to obtain. Only one type of cell can be used for each glass slide. It is not possible, by this means, to study the interaction between cells or the interaction between cells and reagents other than DNA.

Compared with the analytical methods listed above, mass spectrometry constitutes a tool that is much more advantageous in terms of the relationship between the signal detected and the cell phenotype (the molecules expressed by the cell and their respective amounts). It in fact makes it possible to directly measure the amount of proteins present in a sample, without it being necessary to modify the integrity of the molecule (by labeling of the molecule, for example). The principle consists in desorbing from a solid support and ionizing molecules of the sample to be analyzed. Then, the mass/charge ratio of the particles thus created is recorded; it represents the signature of the desorbed molecule.

In the use currently made thereof in cell biology and in proteomics, many sample treatments are necessary (cell lysis, sample purification, introduction of a matrix for MALDI spectrometry, for example), because the specificity and the accuracy allowed for the moment by the instrumentation does not permit a direct analysis of the samples, the quality of which is not controlled to a high enough degree. These treatments introduce biases into the analysis, which is no longer really representative of the cell phenotype.

In addition, the implementation of these methods and the use of the existing equipment allows only a very low sample treatment throughput.

A new system (SELDI for "surface enhanced laser desorption ionization") for using mass spectrometry on more or less complex samples that is a little closer to the cell model, has recently been developed. The asset of this system comes from its ability to perform some of the purifications necessary for obtaining a correct analysis, directly on the support which goes into the machine (selective and oriented adsorption at the surface of the support), which makes it possible to shorten and simplify the sample treatments.

This system is used in particular in the discovery of a disease marker: samples from a sick population are analyzed with respect to others from a normal population, and the differences are analyzed by means of a proprietary program; this makes it possible to identify markers for the disease, and therefore potentially advantageous targets. This method makes it possible to perform really an overall analysis of the samples: the molecules that will be the markers for the disease are not known beforehand.

However, sample treatments are still necessary (cell lysis, washing and purification) in order to obtain good results. For example, the cells are cultured away from the substrate, which implies a non-controlled sample transfer bias. Moreover, the analytical throughput is still low: the chips that can be used in this system can contain only 16 different plots to date.

Several documents concerning mass spectrometry relate to the analysis of living reaction media:

Document US-2002/0160420 describes the analysis by mass spectrometry of a sample of human serum that has undergone several purification steps.

Document US-2002/0076739 describes a method for analyzing proteins in mixtures. Labeled reagents specific for certain peptides are reacted with protein mixtures, and the molecules that have reacted are isolated and then analyzed by mass spectrometry.

Document DE 10038684 describes a method for identifying microorganisms using a MALDI-TOF-MS system, in which the spectrum of a sample of a microorganism to be identified is compared with a database of reference spectra.

Document U.S. Pat. No. 6,531,318 describes a method for analyzing biological tissues, this method comprising a step consisting of microdissection by means of a laser, this microdissection making it possible to select cell aggregates, followed by mass spectrometry analysis.

Document WO 00/48004 describes a device for analyzing cellular material. Cells are cultured, purified by methods other than chromatography, and then injected into a mass spectrometer.

This method requires handling of the cell culture samples; in particular, the purification is a step in the method which eliminates certain constituents of the sample, without the selection of the components that are eliminated being completely controlled.

Document WO 02/103360 describes a method for analyzing proteins at the surface of a cell; this method comprises reacting the cell with a substance at its surface and analyzing it by mass spectrometry.

Document WO 01/65254 describes a method for identifying the chemical structure of a substance present in tissues or cells of various organisms, this method comprising the irradiation of a precise area of a section of living tissue or of a cell, so as to ionize the substance and determine its mass spectrum, and the analysis of this spectrum so as to identify its structure.

Document WO 02/101356 describes a method for analyzing mitochondrial proteins. The proteins constituting the mitochondrion are separated by two-dimensional gel electrophoresis and then analyzed by mass spectrometry.

Document WO 01/84143 describes a method for analyzing a large number of proteins in a small amount of time. Cells are subjected to a stimulation and lyzed, and the samples are divided up so as to obtain batches of a few hundred proteins, and these batches are then analyzed by mass spectrometry using a battery of spectrometers in parallel.

The methods for analyzing living reaction media by mass spectrometry all comprise one or more purification and/or handling steps that result in a loss of information, and/or they imply the search for well-defined molecules, whereas one of the objectives of the invention was that of obtaining an analysis without any constraints regarding the data expressed by the living reaction medium.

In addition, these methods of the prior art, because of the purification and/or handling steps that they comprise, are not very suitable for high-throughput treatment.

BRIEF SUMMARY OF THE INVENTION

By comparison with the techniques of the prior art, the method and the device of the invention have many advantages:

possibility of working on an assortment of varied cells arranged on the same chip,
varied cell systems placed in parallel,
elimination or limitation of steps liable to bias the analysis (such as purification, cell lysis, movement of a sample from one medium to another),
possibility of analyzing a very large number of samples in a small amount of time,
obtaining of data not distorted with respect to the information emitted by the cell.

BRIEF DESCRIPTION OF THE DRAWINGS

FIG. 11 provides an example of a spectrum obtained without CDDP and without TNF. X axis=mass to charge ration in Daltons; Y axis is signal intensity (100 corresponding to the saturation of the detector).

FIG. 12 represents the differences between the spectra of the two phenotypes without TNF and with TNF.

FIG. 13 represents the differences between the spectra of the three phenotypes without TNF or CDDP and with TNF and with CDDP.

DETAILED DESCRIPTION OF THE INVENTION

A subject of the invention is therefore a method for analyzing at least one reaction medium comprising at least one cell C, said method being characterized in that:
(i) the cell C is deposited onto a support S comprising a substantially planar- surface, in the form of an aqueous drop on said surface;
(ii) the substantially planar surface of the support S onto which the aqueous drop containing the cell C has been deposited is optionally covered with a separating film F that allows gases to pass through and prevents evaporation of the aqueous drops deposited onto the support S;
(iii) the cell C is optionally subjected to a stimulation;
(iv) the reaction medium is prepared and introduced into the mass spectrometer;
(v) the reaction medium is desorbed and ionized;
(vi) the mass spectrum of the reaction medium is recorded and analyzed.

A subject of the invention is also a device for analyzing at least one reaction medium comprising at least one cell C, this device being characterized in that it comprises:
a support S comprising a substantially planar surface optionally covered with a separating film F that allows gases to pass through and prevents evaporation of the aqueous drops deposited onto the support S,
means for depositing onto said surface, and optionally under the film F, aqueous drops containing the cell C,
means for desorbing and ionizing the reaction medium,
a mass spectrometer.

The device of the invention may also optionally comprise a controlled-atmosphere chamber in which the support S is placed so as to allow the survival of the cell C.

The stimulation to which the cell C is subjected may vary in nature. It may consist of:
the introduction of a reagent R,
being brought into contact with one or more cells,
a supply of energy,
the application of an electric field or of a magnetic field,
a stimulation by optical treatment.

Figure 1:
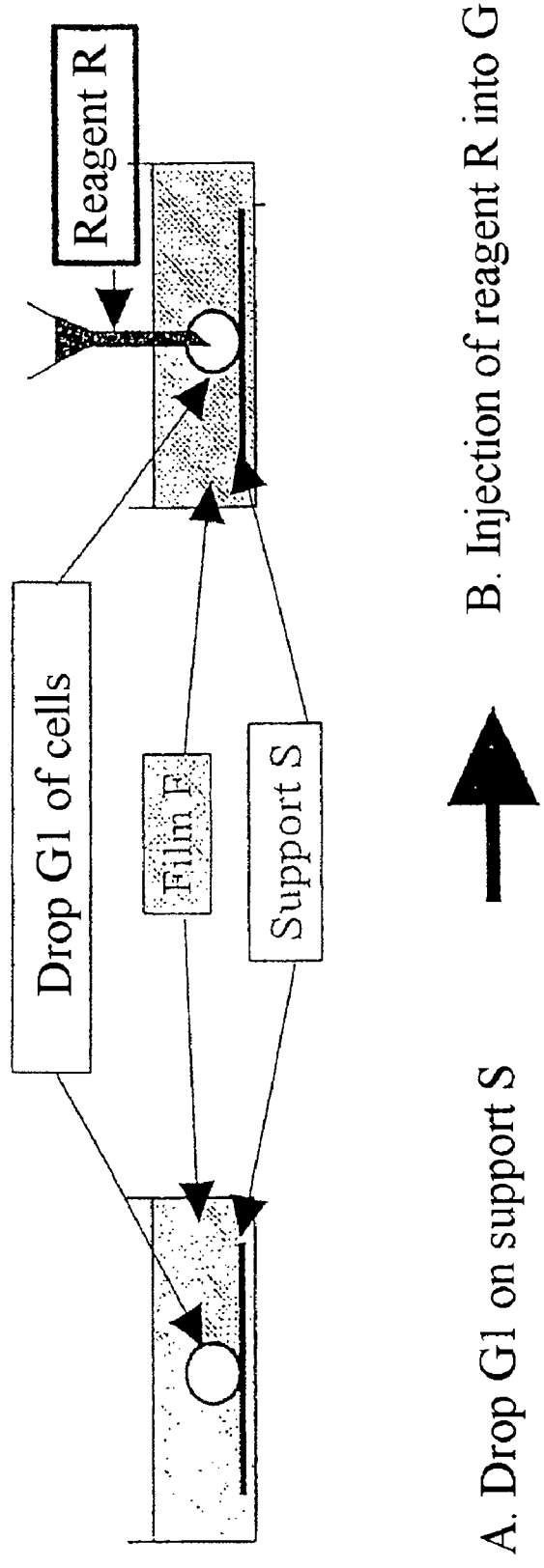
FIG. 1 illustrates transfection by injection of drops: R1 into G1. Drop G1 contains cells; R refers to reagent.
Figure 2:
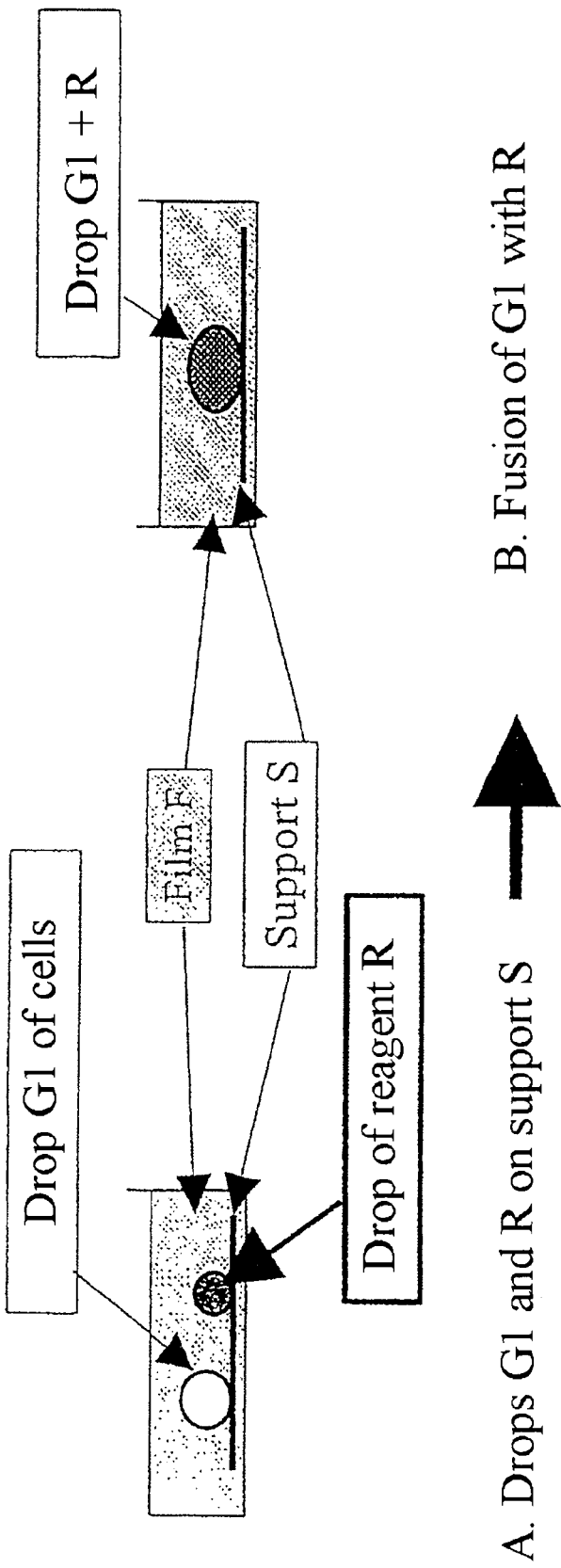
FIG. 2 illustrates transfection by fusion of drops: R1+G1.
Figure 3:
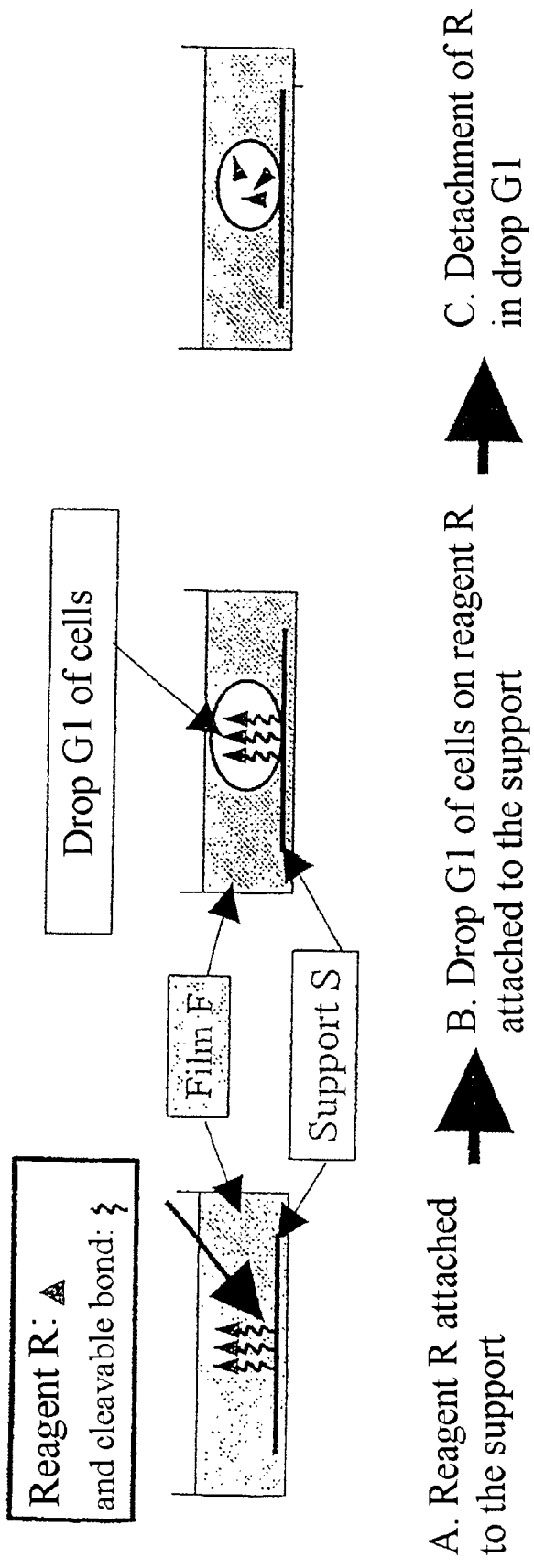
FIG. 3 depicts transfection in drop G1 by detachment of regent R.
Figure 7:
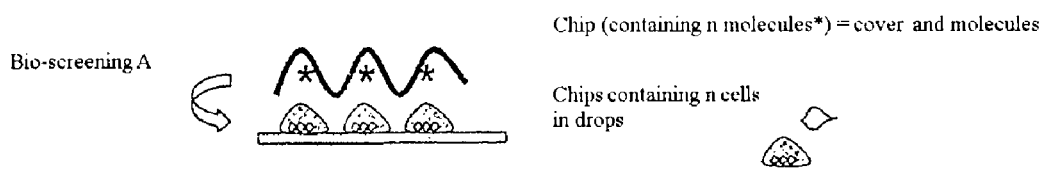
FIG. 7 depicts chip(s) containing n cells in drops.

Several variants exist for the introduction of a reagent R into the cell C:
According to a first variant, an aqueous drop containing the cell C is deposited onto the support S, and a second aqueous drop containing the reagent R is injected, using any suitable injection means, directly into the drop containing the cell C. Such a variant is illustrated in FIG. 1.
According to a second variant, a first aqueous drop is deposited onto the support S and then a second aqueous drop is deposited onto the same support in proximity to the first; one of these drops contains the cell C, the other the reagent R, and the reaction of the reagent R with the cell C and, optionally, its transfection into the cell C is triggered by the fusion of the two drops. The displacement and the fusion of these drops can be obtained by vibration within the support, by electrophoretic displacement of the electrically charged drops or by means of mechanical or optical clamps. It can also be obtained by a modification of the surface properties of the support, brought about by the application of an electric or magnetic field, or by a suitable thermal or optical treatment. Such a variant is illustrated in FIG. 2.
According to a third variant, the reagent R is attached to the support S or to the film F, the cell C is deposited in the form of an aqueous drop onto the support S and the reagent R is then detached from the support S or from the film F in order to allow it to react with the cell and, optionally, to be transfected into the cell. This variant is illustrated in FIGS. 3 and 7.

In the present invention, the term "transfection" is used to denote the penetration of a molecule of a reagent, whatever it may be, into a cell.

When the stimulation of the reaction medium comprises the introduction of a molecule of a reagent R, the separating film F, when it is present, is chosen so as to be non-miscible with R.

Among the means for supplying energy, mention may in particular be made of thermal treatment means, which may consist, for example, of a heating device that can be placed in proximity to the support S or attached to this support and that is intended to bring the droplets to an appropriate temperature. For example, the heating means may consist of electrically conducting wires that also serve as a means of receiving the drops.

The optical treatment means are in particular means for treatment with ultraviolet rays, the latter being known to induce crosslinking between complementary strands of DNA and between DNA and proteins.

The bringing into contact with one or more other cells consists in introducing one or more other cells into the reaction medium so as to constitute a network of cells capable of interacting.
According to a first variant, an aqueous drop containing the cell C is deposited onto the support S, and a second aqueous drop containing one or more other cells is injected, using any suitable injection means, directly into the drop containing the cell C. The order of deposition of the drops of cells can of course be reversed.
According to a second variant, a first aqueous drop is deposited onto the support S and then a second aqueous drop is deposited onto the same support in proximity to the first; one of these drops contains the cell C, the other drop containing one or more other cells, and the interaction between the cells is triggered by the fusion of the two drops. The displacement and the fusion of the drops can be obtained by vibration within the support, by electrophoretic displacement of the electrically charged drops or by means of mechanical or optical clamps. It can also be obtained by modification of the surface properties of the support, brought about by the application of an electric field, of a magnetic field, of a thermal treatment or of an optical treatment.

Preferably, the support S consists of a plate that can be made of silicon, of glass or of a polymer, for instance of polyurethane, nylon, polyester, polyethylene, polypropylene, polyfluorocarbon, poly(methyl methacrylate) (PMMA), polycarbonate, polyvinyl chloride (PVC), polydimethylsiloxane (PDMS) or polysulfone.

According to the invention, the attachment of the drops to the support occurs due to surface tension forces. Preferably, the support S has a substantially planar surface comprising at least one means for receiving the aqueous drops.

Preferably, the means for receiving the aqueous drops consists of areas of the substantially planar surface of the support S that range from 5 µm$^2$ to 5 mm$^2$ in size.

According to a first variant, it may be envisioned that the support S exhibits a hydrophobic nature on its planar surface and comprises one or more hydrophilic areas constituting said receiving means. According to another variant, it can also be envisioned that the support S comprises, on its planar surface, cavities that range from 1 micron to 1 millimeter in depth and constitute said receiving means. It can also be envisioned that the support S is a plate that has outgrowths of small thickness, from 1 micron to 1 millimeter, arranged on its surface and intended to promote the attachment of the drops. Finally, it can be envisioned that the support S is a plate that has at least one wire onto which the drops attach. The depositing of two drops onto the same receiving means will promote the fusion of these two drops and therefore the reaction of the reagent R with the cell C. Preferably, the support S exhibits a hydrophobic nature on its planar surface and comprises one or more hydrophilic areas constituting the receiving means. In order to confer a hydrophobic nature on the planar surface of the support, said surface is preferably covered with a hydrophobic substance such as a polyfluorocarbon, for instance polytetrafluoroethylene or Teflon®, or a silane, for instance perfluorosilane. The hydrophobic area of the support can consist of a surface structuring that is indented on a nanometric scale, such as the "black silicon" used in optics.

Examples of commercial slides of this type are the superteflon 40-well D2 mm immunofluorescence slides sold by the company Merck Eurolab division Polylabo.

Figure 6:
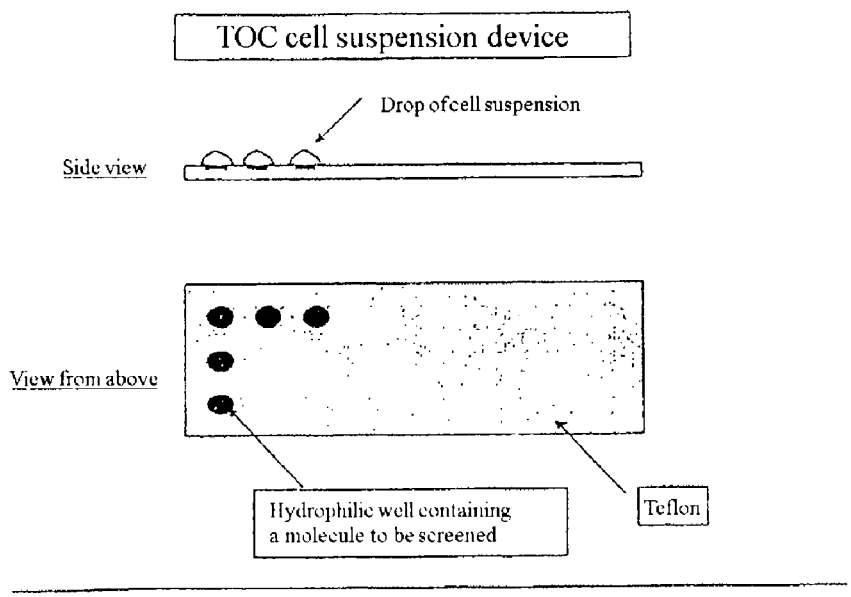
FIG. 6 shows a side view and view from above of a TOC cell suspension device.

Even more preferably, the support also comprises a second means for receiving the drops, superimposed on the first, such as, for example, a hydrophobic planar surface and hydrophilic outgrowths of small thickness, or a hydrophobic planar surface and hydrophilic wells, as illustrated in FIG. 6, or a hydrophobic planar surface and a hydrophilic wire.

The support may be adapted from a support used conventionally for mass spectrometry; it may be envisioned that it comprises a layer that may be electrically conducting (steel, for example) or not; that it is covered, at least on the receiving means, with a substance that promotes desorption. Such supports exist on the market, for example:

- the SELDI chips ("ProteinChip® arrays") sold by the company Ciphergen Inc. (model NP20, for example) comprise a thin hydrophobic layer pierced with holes where the surface is active (hydrophilic);
- the "Anchor Chip™" supports sold by the company BrukerDaltonics Inc. comprise hydrophobic surfaces on which hydrophilic outgrowths are placed.

The supports may also be active, so as to cause the drops on its surface to change, using the principles of droplet microfluidics. This amounts to dynamically modifying the surface properties of the support (for example, variations in surface tension/energy) so as to cause the drops to move in a controlled manner. Thus, the drops of cell cultures can go through various reaction steps carried out within the support: it is possible to fuse two drops which are close together (one with the reagent and another with the cells, for example).

To produce this type of support, Shenderov et al. ("Electrowetting-based actuation of liquid droplets for microfluidic applications", Applied Physics Letters, vol. 77, No. 11, p. 1725-1726, September 2000) describes the use of the modification of the surface energies of a hydrophobic layer when an electric field is applied: the surface tension decreases with the strength of the field, the surface becomes less hydrophobic, or even hydrophilic. The control and the movement of the electric field makes it possible to displace the drops of liquid on this surface. This method was patented by the company Nanolytics (Shenderov et al. "Actuators for microfluidics without moving parts", No. U.S. Pat. No. 6,565,727; 2003), but without the use of cell cultures.

Another manner in which these surface properties can be modified consists of the physicochemical modification of the surface layer of the support, still using an electric potential. For example, the change in conformation of an SAM layer ("self-assembled monolayer", for example modified thiols, comprising at least one hydrophilic end and one hydrophobic chain), demonstrated by Lahann et al. ("A reversibly switching surface", Science, Vol. 299, p. 371-374, January 2003), makes it possible to go from a straight conformation of the molecules within the surface layer, which then is hydrophilic in nature, to a curved conformation, in which it is hydrophobic in nature.

Similarly, the temperature can be used as a means of changing the surface properties of a support. Liang et al. ("Preparation of Composite-Crosslinked Poly(N-Isopropylacrylamide) Gel Layer and Characteristics of Reverse Hydrophilic-Hydrophobic Surface" Journal of Applied Polymer Science 72:1, 1999) describes a polymer which is hydrophilic at low temperatures (<30° C.) and hydrophobic above this. By integrating a system of localized control of the temperature under the substrate, it is possible to control the surface properties.

It is also possible to set up a support for which the properties of the surface layer change according to whether or not light is applied (electromagnetic field). Ichimura et al. ("Light-driven motion of liquids on a photoresponsive surface", Science, Vol. 288, p. 1624-1626, June 2000) describes such a surface: a layer of polymer (calyx[4] resorcinarene), the terminal group of which (azobenzene) can change isomeric conformation after asymmetric photoirradiation. When these cyclic groups in the trans conformation (hydrophilic layer) are exposed to UV radiation (365 nm), they change to the cis conformation (hydrophobic). The reaction is reversible using blue light (436 nm). By selectively and gradually lighting the polymer layer, it is possible to displace liquid drops in a controlled manner.

According to a variant of the invention, the reagent R is attached to the support S before depositing of the aqueous drop containing the cell C. Such devices are known to those skilled in the art for other uses: they are the DNA chips as described by:

- Eisen M. B., Spellmann P. T., Brown P. O., Botstein D. Cluster analysis and display of genome-wide expression patterns, *Proc Natl Acad Sci USA*. 1998 Dec. 8; 95(25); 14863-8;
- Haab B. B., Dunham M. J., Brown P. O., Protein microarrays for highly parallel detecting and quantitation of specific proteins and antibodies in complex solutions, *Genome Biol*. 2001 Jan. 22; 2(2): RESEARCH 0004.1-0004.13;
- Livache T., Bazin H., Caillat P., Roget A., Electroconducting polymers for the construction of DNA or peptide arrays on silicon chips, *Biosens Bioelectron*. 1998 Sep. 15; 13(6): 629-34.

The same principle can be applied to molecules other than polynucleotides. Molecule chips are described in: Kuruvilla et al., Glucose signalling with small molecule microarrays, *Nature* (2002), 416 p. 653. In all cases, the reagent molecule is first attached to the chip (for example by covalent attachment to a glass slide). According to the present invention, the molecule may optionally be detached after depositing of the aqueous drops containing cells onto the molecule chip.

Figure 5:
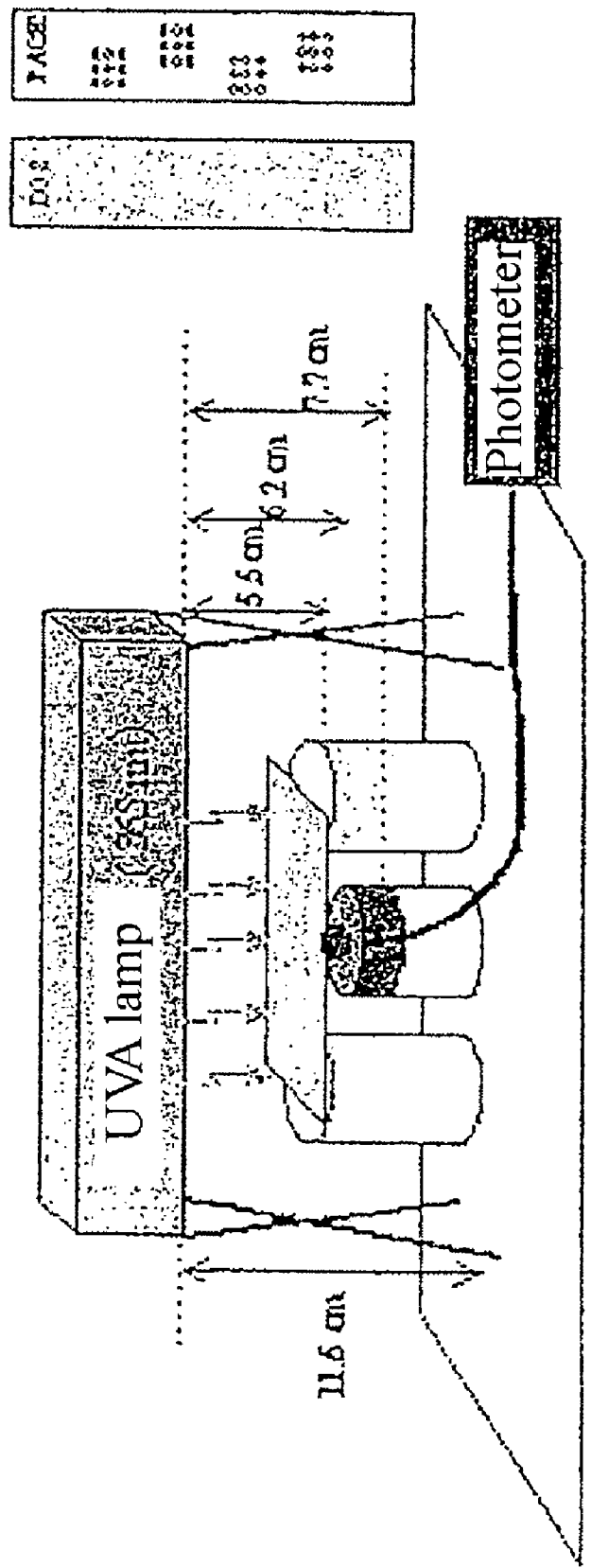
FIG. 5 illustrates a photocleavage device.

The detachment of the reagent molecule can be carried out in a known manner by one of the following means:
UV-photocleavage using a site for binding of the reagent to the support which is photocleavable, as illustrated in FIG. 5.
In addition, when the reagent is a polynucleotide only:
cleavage of the double-stranded DNA with restriction enzymes, or with other nucleases,
modification of the hybridization stringency: a change in salt concentration, in temperature or in redox conditions of the medium makes it possible to separate two DNA strands.
In certain cases, it is envisioned that the reagent R remains attached to the substrate.

According to the invention, the substantially planar surface of the support S may be covered with a separating film which performs three functions:
it must prevent unwanted fusion of the aqueous drops,
it prevents evaporation of the aqueous drops deposited onto the support,
it allows gases to pass through, in particular $O_2$ and $CO_2$, the latter two functions being intended to allow the cells to survive in their drops.

The film F may be varied in nature:
it may be a non-water-miscible liquid such as, for example, an oil. Up until now, it was known how to use oil to preserve certain cells; however, it had never been used to carry out reactions on cells. Among the oils that can be used in the method and the device according to the invention, mention may in particular be made of mineral oils and silicone oils. It is also possible to use, as liquid, an organic solvent that is non-miscible with the compounds to be treated (cells and reagents), such as, for example, octane. A light mineral oil is preferably used;
it may also be a gas such as air saturated with moisture;
it may subsequently be a flexible, solid film, such as a PDMS (polydimethylsiloxane) film or a nitrocellulose film;
finally, it may be a rigid honeycombed cover made of porous material, the size of the cavities being adjusted so as to be able to contain the drop of cell(s) and, optionally, of reagent. According to a variant of the invention, the rigid honeycombed cover may be functionalized, in each cavity, with a reagent molecule and may thus constitute a molecule chip or a nucleotide chip destined to come into contact with the support onto which drops of cells have been deposited in a manner that is symmetric with respect to the cavities. This variant of the invention is illustrated in FIG. 7.

Before introduction of the reaction medium to be analyzed into the mass spectrometer, the separating film, if it is liable to impair the implementation of the steps of this analysis, is removed.

When there is no separating film or when the latter is a gas or a liquid, the aqueous drops containing a cell or a reagent are advantageously deposited onto the support S, and optionally under the separating film, by means of fine capillaries, as illustrated in FIG. 1. Preferably, these capillaries are connected to a pump or syringe pump making it possible to control the volume of the drops.

The cells and the reagents can also be dispensed by means of a conventional system such as those used for the fabrication of DNA chips. Mention may, for example, be made of piezoelectric systems for compressing a cavity and ejecting a drop via a nozzle. Reference may be made, on this subject, to N. Takada et al., Proceeding of the SID, Vol. 27/1, 1986, 31-35.

Preferably, the ejected drops pass through the liquid or gas film by virtue of their rate of ejection and/or by gravity, this liquid or this gas being lighter than the solution to be deposited. When the separating film is a solid film or a rigid cover, it is deposited onto the support, after depositing of the aqueous drops of cells and, optionally, of reagents, by the same means as described above.

The displacement and the fusion of the drops can be obtained by vibration within the support, by electrophoretic or electromagnetic displacement of the electrically charged drops or by means of mechanical or optical clamps. It can also be obtained by modification of the surface properties of the support, brought about by the application of an electric field or of a magnetic field, by thermal treatment or optical treatment, etc.

Preferably, the support S of the device is mobile, so as to allow it to move from a first depositing means to a second depositing means, and optionally to other depositing means, and also so as to allow it to move to the mass spectrometer. The support S may, in certain cases, consist of a solid film attached to rollers at its two ends, the rollers being equipped with winding means so as to allow displacement of the film and therefore displacement of the drops which have been deposited on it.

Generally, the method according to the invention envisions the displacement of the support S after the depositing onto the support S of the first series of drops, regardless of whether they are drops of cells or drops of reagent.

According to the invention, the support S may be placed in a controlled-atmosphere chamber, the temperature, the hygrometry and the $CO_2$ content of which are adjusted so as to allow the cells to survive.

Such devices are in particular controlled-atmosphere incubators. The temperature in such a device can range from 35 to 42° C., a preferred temperature being between 36.5 and 37.5° C. Temperature variation may in particular be used to induce cell differentiation.

The $CO_2$ level is preferably maintained at between 3 and 5%. The oxygen $O_2$ level is preferably that of ambient air.

For example, it is possible to envision maintaining the cells in aqueous drops on the support S in an incubator at 37° C., with 95% air, 5% $CO_2$ and 97% humidity.

It is generally envisioned that only the supports onto which have been deposited the drops of cells and the separating film are placed in a controlled-atmosphere chamber. However, other elements of the device of the invention can, if necessary, be placed in this chamber.

Advantageously, it is possible to envision that the aqueous drops containing one or more cells, a cell tissue or a cell network comprise a culture medium.

In fact, the establishment of cell cultures depends on the ability of the cells to maintain their proliferation and therefore on the conditions essential to their growth.

Advantageously, it is envisioned that the aqueous drops of cells comprise MEM, or minimal essential medium, sold by Gibco BRL under the Cat. reference No. 12000-022.

The culture medium may also contain other constituents, such as calf serum, one or more antibiotics intended to control the sterility of the medium, for instance penicillin.

It is also possible to envision using, in the culture medium, chemical agents which induce cell differentiation, for instance bromodeoxyuridine.

It is also possible to envision that the aqueous drops in which the cells C are cultured are gelled, using any known gelling agent, for instance agar or gelatin.

Advantageously, the aqueous drops containing the cell(s) or the cell tissue or the cell network, and/or the aqueous drops containing the reagent, comprise one or more constituents intended to promote transfection, for instance liposomes. Such transfection agents are described in particular in documents WO 01/20015 and WO 98/33932.

Other means intended to promote transfection can also be used in the device of the invention, such as: electroporation or microprecipitation. These transfection methods, which are well known to those skilled in the art, are described in particular on http://opbs.okstate.edu/~melcher/MG/MGW4/MG43.html.

It can also be envisioned that the device comprises means of detection focused on one or more drops deposited onto the support.

The means of detection are in particular devices intended to measure the fluorescence or the radioactivity of one or more drops or of the cells contained in one or more drops.

The means used in the devices according to the invention will preferably be connected to a control device making it possible to automate the device and the method according to the invention.

The use of the device and/or of the method according to the invention has many advantages: very small amounts of materials can be used: a single cell per drop makes it possible to carry out a transfection experiment and is sufficient to perform a mass spectrometry analysis. It is possible to work with very small drop volumes, of less than 1 microliter, preferably of 0.1 to 1000 nanoliters containing 1 to 500 cells, even more preferably of 0.1 to 10 nanoliters containing 1 to 10 cells. Advantageously, drops containing from 1 to 100 cells are used. It is also possible to envision working on larger volumes, in particular greater than a microliter (10 to 100 μl, containing 500 to 100 000 cells). This method also makes it possible to use small amounts of reagent. The separating film F makes it possible to control the gas exchanges of the culture medium of the cell and its sterility. It also makes it possible to separate drops that are not intended to react together. The cell cultures in the form of drops under the separating film can be conserved for at least 24 hours and for up to several days without any notable modifications of their cellular activity being observed (without notable influence on the proliferation and growth of the cells).

The method and the device according to the invention also make it possible to carry out batteries of reactions:

Several aqueous drops each comprising at least one cell can be deposited onto the support S, said drops being isolated from one another. Preferably, each of these drops is placed in a different receiving means. All the cells may be identical, but it is also possible to envision placing different cells (at least two sorts of different cells) in the various drops. Drops containing the reagent(s) are deposited in proximity to each drop containing a cell so as to allow the fusion of one drop containing the appropriate reagent with the drop containing the targeted cell. It is also possible to envision injecting a drop of reagent directly into each drop of cell. For carrying out batches of reactions, a support comprising means for receiving the drops, arranged evenly in the form of matrices, is advantageously envisioned so as to allow the method to be automated.

Advantageously, the support and the capillaries intended to deposit the aqueous drops of cells and of reagents are connected to control means so as to allow the method to be automated.

The method and the device according to the invention therefore make it possible to carry out, simultaneously and in an automated manner, a large number of reactions of a reagent on a cell, varying the nature of the reagent and of the cell, while at the same time working on extremely small volumes, and then to analyze the result of these reactions.

Among these cells that it may be advantageous to study by means of this method, mention may in particular be made of:
primary cells,
hybridomas,
cell lines: the cells can perpetuate endlessly and thus form lines,
stem cells: they are obtained from a sample taken from an animal or from biopsies,
a piece of cell tissue (the cells are not individualized),
mixtures of the various types of cells stated above.

The cells are cultured in (aqueous) culture medium in a known manner. It is also possible to culture heterogeneous cells for several days and to use this mixture.

According to a variant of the invention, when all the cells to be reacted on the same support are identical, the procedure may be carried out in the following way: the support is a hydrophobic plate comprising hydrophilic areas, it is immersed in an aqueous solution containing the cells, and then it is removed from this solution, allowing the excess liquid to run off. The drops of the medium containing the cells are retained in the hydrophilic areas. This step is followed by the depositing of a layer of separating film F and by the depositing of the drops containing a reagent or other cells. Depending on the nature of the film F (fluid or solid), it is deposited before or after the depositing of the drops of reagent or of other cells.

Among the reagents R that can be used in the method and the device according to the invention, mention may be made of:

Chemical molecules of all natures, in particular inorganic molecules, natural organic molecules, molecules derived from organic synthesis and from combinatorial synthesis, molecules extracted from biological samples, and molecules extracted from biological samples, that have been modified by synthesis. Mention may in particular be made of polynucleotides: single-stranded and double-stranded RNA molecules, single-stranded and double-stranded DNA molecules; PNA (peptide nucleic acid) molecules, which are peptide-nucleic acid chimeras; ribozymes; double-stranded interfering RNAs or proteins and peptides. Among the proteins, mention may most particularly be made of transcription factors.

The reagent molecules can be formulated in a solution ready to be deposited. They can also be prepared directly after depositing onto the support, for example by synthesis, in particular by organic synthesis, in situ, or by in vitro transcription in the drop. Prion-type molecules can also be obtained in the drop by peptide polymerase chain reaction or PCR before transfection thereof into the cells. When nucleic acid molecules are used, they can be prepared by nucleic acid PCR. As has already been disclosed above, the reagent can also be attached to the support.

When DNA is used as reagent, it is advantageously in precipitated form. Calcium phosphate can, for example, be used in a known manner. The DNA precipitation can also be carried out in the aqueous drop deposited onto the support, by fusion with a drop of the appropriate reagent.

Figure 4:
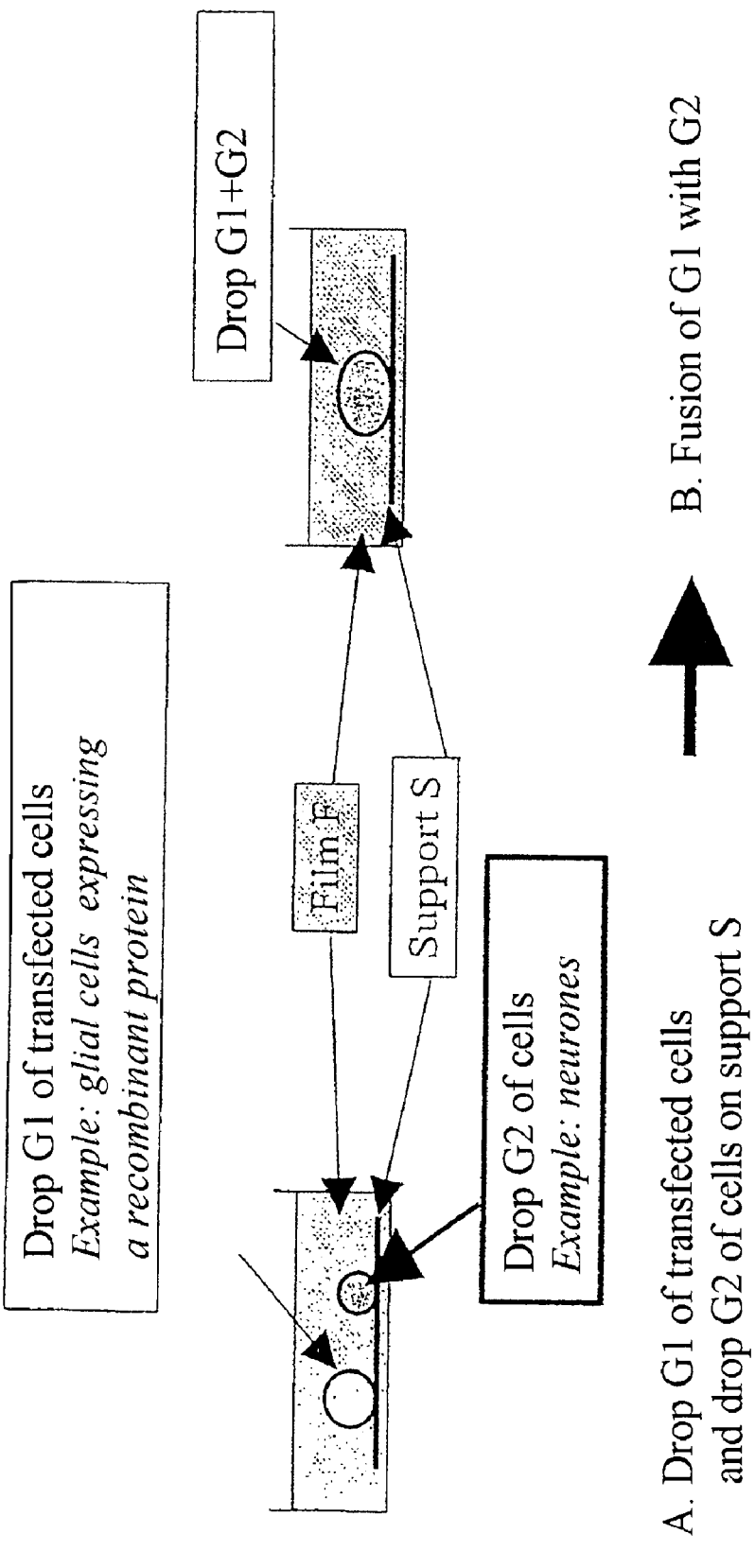
FIG. 4 shows fusion of cell drops G1+G2 after transfection.

According to a variant of the device and of the method according to the invention, it is possible to envision making several successive deposits intended to be fused:

It is possible to envision successively depositing several reagents intended to transfect the same cell, and observing their cumulative effects;

It is also possible to envision depositing several drops of cells and causing them to fuse, so as to reconstitute a cellular network of identical or different cells in order to be as close as possible to conditions encountered in vivo. For example, it is possible to reconstitute networks of neurons on the scale of a few cells, by means of glial cells encountering neurons, so as to make them communicate within the same drop as illustrated in FIG. 4, or interactions between various types of cells which make up the skin, in order to mimic the behavior thereof on a cellular scale.

It is also possible to reconstitute a cellular tissue intended to mimic the behavior of the epidermis by culturing together, within the same drop, keratinocytes on a layer of collagen. It is also possible to culture together skin stem cells in the presence of hair follicle cells in order to study their interactions.

For example, it is possible to use the transfection of reagents into a first type of cells in order to trigger a cellular reaction, such as the production of a recombinant protein, and then to react this first cell population with a cell population of another type by fusion with another drop.

Figure 8:
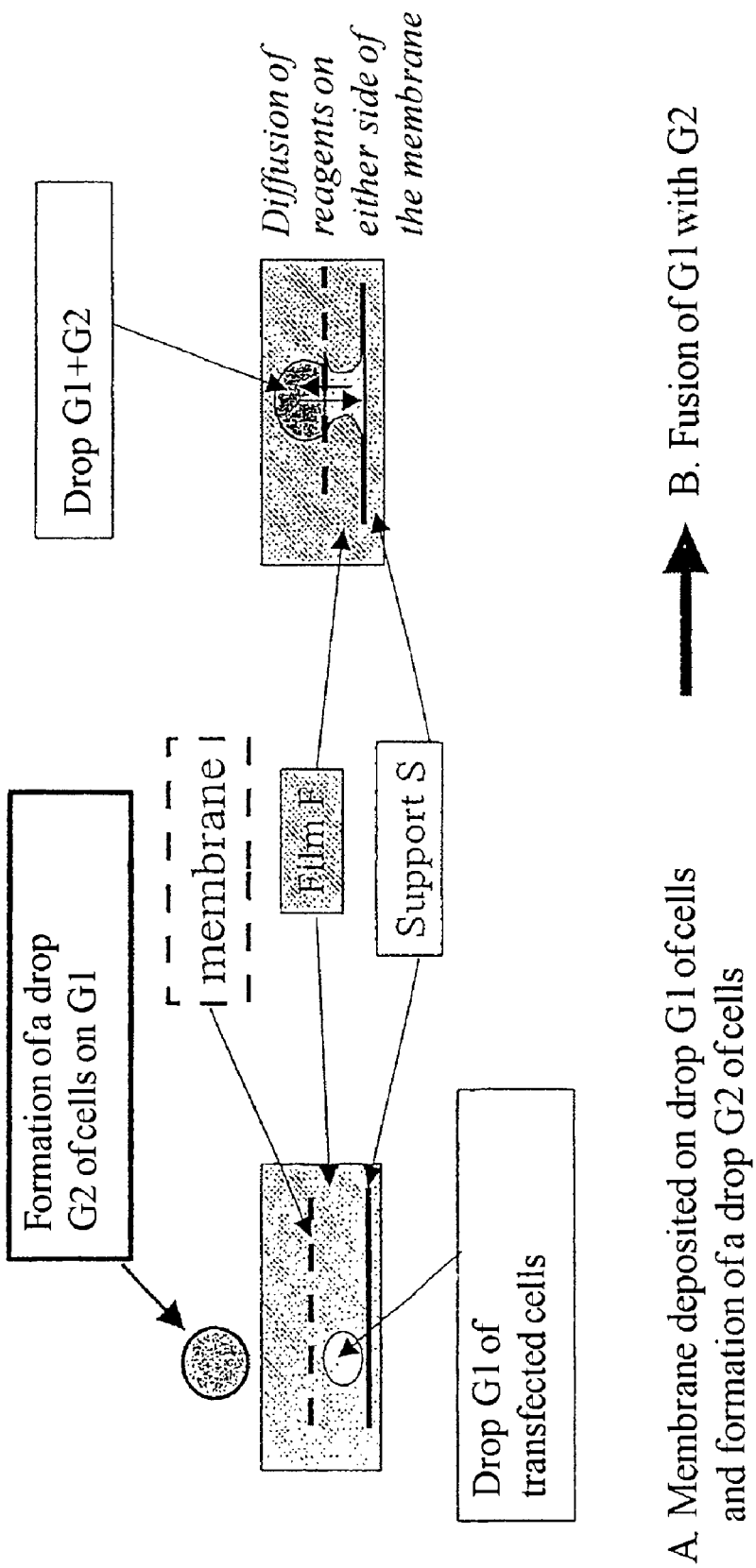
FIG. 8 illustrates a membrane between two cell drops G1 and G1.

According to a variant of the invention illustrated in FIG. 8, it is also possible to envision that the support is equipped with separating means that make it possible to separate two different cell types but that permit the passage of small molecules between these cells. Such a separating means is intended to mimic a biological barrier, such as, for example, the barrier that exists between the blood and cervical cells. Such separating means are advantageously arranged on the receiving means, on the support. In order to use them, it is envisioned to deposit an aqueous drop comprising at least one cell of a first type onto one side of the separating means and an aqueous drop comprising at least one cell of a second type onto the other side of the separating means. The fusion of the drops on either side of the separating means allows communication between the cells by means of molecules capable of diffusing through the separating means. This communication can then be studied by any means, in particular by the addition of reagents in the form of an aqueous drop before or after the fusion of the cell drops. Through the automated transfection of these drops, it is possible to analyze the biological role of the factors transfected in a biological multilayer.

The separating means that can be used according to this variant of the invention are artificial membranes such as, for example, a nitrocellulose filter, silicon pierced with nanoholes, blotting paper, a cloth filter; the use of a solid gel, such as an agarose, collagen or gelatin gel, can also be envisioned.

The device and the method according to the invention make it possible to study the automated expression of recombinant proteins obtained by the entry of coding DNA into cells, to carry out the screening of nucleic acid molecules intended to modify (to block or, on the other hand, to increase) gene expression in cells, and to search for genomic promoter sequences. This invention also makes it possible to study the interactions between cells of different types, this interaction being triggered by the mixing of the drops. The device and the method according to the invention make it possible to obtain an overall view of the biological effects of the reaction of molecules of all types with cells, and in particular of the automated entry of molecules of all types into cells.

According to a variant of the invention, it is possible to envision one or more steps consisting in treating the reaction medium directly on the support S before its introduction into the mass spectrometer. These treatment steps can consist of a cell lysis, one or more washes, the adsorption or the attachment of molecules that have an affinity for molecules whose presence it is intended to detect.

Next, the reaction medium placed on the support S is prepared with a view to introducing it into the mass spectrometer.

This preparation may consist in freezing the reaction medium so as to preserve its characteristics. It may consist in drying, with or without thermal treatment, with or without vacuum, for instance by lyophilization. It may also be envisioned to fix them by treatment with an agent such as methanol or formaldehyde. The application of several successive preparation steps may be envisioned.

According to the method of the invention, when the mass spectrometer is of the MALDI type, the preparation of the reaction medium with a view to introducing it into the mass spectrometer comprises, in a known manner, the addition of one or more acid molecules that are small in size and absorb light, for instance alpha-cyano-4-hydroxycinnamic acid, nicotinic acid or sinapinic acid. Said molecule in solution is added to the reaction medium to be analyzed such that, after drying, the sample to be analyzed is included in the crystalline matrix formed by this molecule, which makes it possible to ensure successful desorption and ionization of the sample.

The solution of molecule intended to form the crystalline matrix is advantageously added to the reaction medium in very large molar excess so as to promote the formation of the crystalline matrix during the air-drying of the entire mixture. When another type of spectrometer is employed, other molecules that promote desorption are used, in a manner known to those skilled in the art.

The reaction medium is then desorbed and ionized. This step is carried out with a means of desorption selected from: a laser beam, a beam of ions, a beam of neutral atoms, a beam of electrons. The desorption/ionization can also be carried out by spraying of a liquid sample. The resolution is of the order of the size of the beam and allows very precise targeting of the reaction medium that it is desired to desorb. When a plurality of reaction media are on the support S, each of the deposits can be targeted, and therefore desorbed/ionized, successively.

Each of the reaction media deposited onto the support S is desorbed and ionized individually and its mass spectrum is also produced in an individual and targeted manner.

The support S is placed in the mass spectrometer and each of the reaction media placed on this support is treated individually. The same reaction medium can be treated several times (several thousand laser treatments) so as to give a more complete analysis of the phenotype under consideration.

The arrangement of the deposits on the support S in the form of a matrix allows the desorption and ionization to be automated.

Mention may be made of the following known systems as means of desorption/ionization:
  MALDI: matrix assisted laser desorption ionization and its counterpart of the
  SELDI: surface enhanced laser desorption ionization
  SIMS: secondary ion mass spectrometry
  SNMS: secondary neutral mass spectrometry
  ESI: electrospray ionization
  FAB: fast atom bombardment
  APCI: atmospheric pressure chemical ionization.

Mention may be made of the following known systems as means of measuring mass:
  TOF: time of flight,
  MS/MS: tandem mass spectrometry or multidimensional MS for MS/MS/MS/etc.,
  quadrupole (or ion trap),
  FT-MS or FT-ICR: Fourier-Transform mass spectrometry-ion cyclotron resonance.

Any combination of these various means comprising at least one means of desorption and one means of analysis can be considered according to the present invention as a mass spectrometer.

The mass spectrum obtained for each reaction medium can be compared with a database of mass spectra so as to allow the identification of known molecules within the reaction medium.

The comparison of the mass spectrum of a cell culture with that of a reaction medium derived from this culture makes it possible to identify modifications that have been involved in the cell culture subsequent to the stimulation that was applied to it.

The change over time in the response of a cell or of a set of cells to a given stimulation can be studied by means of the method and the device of the invention: the same stimulation can in fact be applied at intervals over time to a series of identical reaction media placed in series on the same support S.

Figure 10:
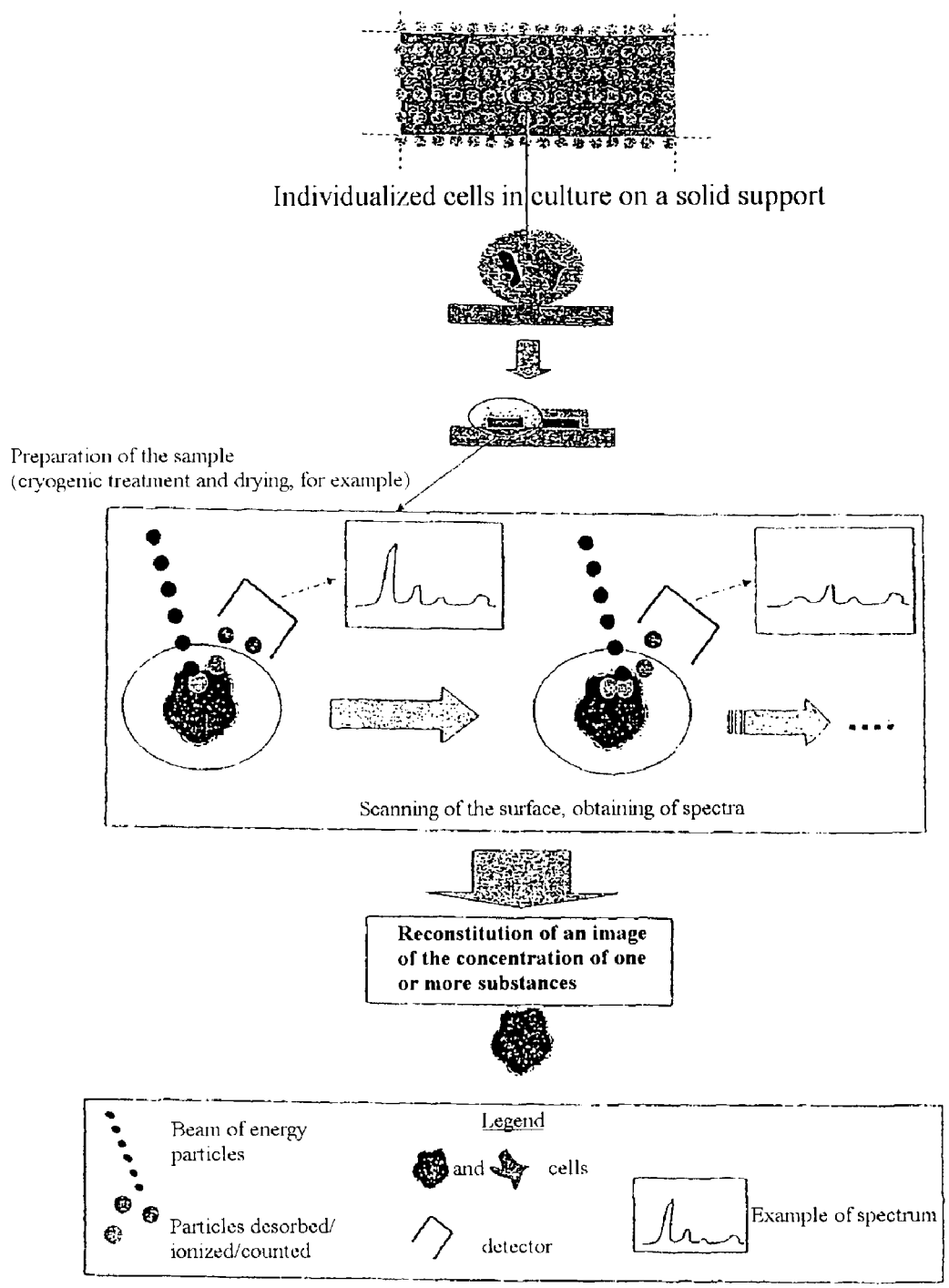
FIG. 10 depicts reconstitution of an image of the concentration of one or more substances.

The method and the device of the invention make it possible to perform mass spectrometry imaging: the molecules present in the sample are desorbed/ionized selectively on an area that is small in size (less than 100 μm—of the order of the size of the beam used), sequentially over the entire surface of the sample. For each "point" of the surface a spectrum is then obtained which describes the relative abundance (concentration) of molecules present in this point of the sample. The abundance of a molecule is represented by the height of a peak (or the area of the curve under this peak) within the spectrum obtained. If one peak is selected in all the spectra, it is possible to envision recreating an "image" of the sample relative to this molecule, in the same way as for a fluorescence scanner: a point is represented, for example, by a pixel of color, associated with a color code which makes it possible to evaluate the abundance of the molecule described by the peak selected at this point; the set of pixels gives a readily interpretable image. This variant of the invention is illustrated in FIG. 10.

This process can be implemented for each of the peaks present in the spectra, and therefore, from a single scan of the surface by the beam, it is possible to recreate an image of the sample for each molecule of interest detected in the sample. An analysis by fluorescence scanner generally only makes it possible to visualize molecules labeled prior to the scanning, in a sequential manner (one labeling for one molecule and for one scan).

It is also possible to select several peaks for the entire sample, each represented by a color, which is more or less intense according to the abundance of the molecule. The superposition of the two colors gives an image of the ratio of concentration of the substances with respect to one another.

The method and the device of the invention make it possible to perform the overall analysis of a sample:

The cell cultures are prepared for their introduction into the spectrometer (drying, cryogenic treatment, addition of a matrix for promoting desorption/ionization, for example). The sample is scanned overall by the beam. A large number of spectra are recorded, which are added to give a mean of the abundance of the various substances in the sample.

Figure 9:
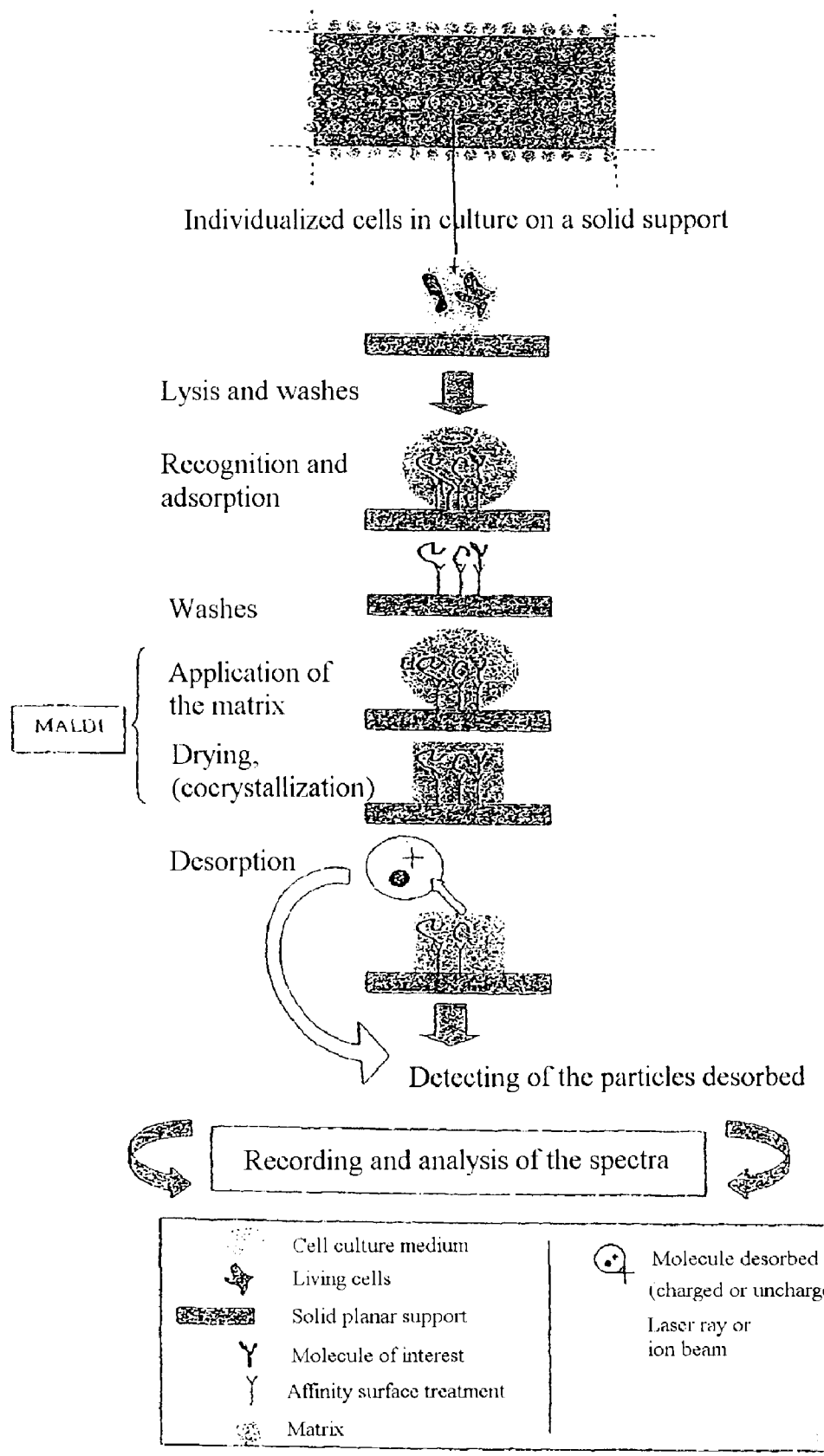
FIG. 9 depicts washing and simplification steps prior to spectrophotometry.

The method and the device of the invention make it possible to perform the overall analysis of a simplified sample:

In order to facilitate the analysis of the spectrum obtained during overall scanning of the surface, it is possible to simplify the sample, directly on the chip, before it is introduced into the spectrometer, using active surfaces. These surfaces can make it possible to more or less specifically retain certain substances of the sample, subsequent to washing as illustrated in FIG. 9.

The method and the device of the invention make it possible to study the change in a living reaction medium under the effect of a stimulation. This approach does not require the modifications (protein expression, for example) engendered by this stimulation to be known beforehand, as is the case for the other methods for analyzing reaction media in a matrix. In addition, all the reactions that occur take place in the living cell, in the presence of the same influencing factors as in an in vivo test. Finally, the manipulations and treatment consisting of purification and/or of extraction and/or of transfer of the reaction medium can be avoided with the method of the invention, which makes it possible to avoid the artifacts and the biased observations that are specific to in vitro study systems.

More specifically, the device of the invention comprises at least one piece of equipment for measuring the mass of a sample by means of mass spectrometry, said piece of equipment comprising a spectrometer tube, a device for creating a vacuum in said tube, electrical means for applying an electrical acceleration potential in the tube so as to accelerate the molecules of the sample to be analyzed, a means for detecting the mass of the ions formed, a means of introducing the support S into the tube so as to allow the introduction of the reaction media associated with molecules for promoting desorption in the spectrometer, and a means for the desorption and the ionization of some of the molecules of this sample.

Said means for desorption and ionization is connected to a data acquisition system so as to allow the sequenced treatment of a plurality of samples to be analyzed, placed on a support S in the form of a matrix or chip.

The method of the invention comprises the following steps:
  treatment of the living reaction medium or media placed on the support S with a means that promotes desorption so as to produce samples ready to be analyzed;
  introduction of the samples (reaction media) placed on the support S into the mass spectrometer tube; application of a vacuum and of an electric field in the spectrometer introduction tube so as to form an acceleration potential; application of a desorption/ionization treatment, in a controlled and sequenced manner, to the sample(s); detection of the mass of the ions formed; optionally, comparison of the data recorded with a mass spectrum bank.

The method and the device of the invention have many advantages:

This technology in fact makes it possible to realize thousands of independent experimental conditions on a miniature format.

The microdrop format allows a vigorous control of the culture conditions of the cell model throughout the various processes implemented. This control is strengthened by the integration of all the sample treatments directly on the chip, possibly by means of surface chemistry: culture, stimulation, purification (optionally).

So as not to compromise this control, as for all the existing methods, no sample transfer is carried out between the culturing steps and the recording of the final signal.

This recording takes advantage of the accuracy and the specificity of mass spectrometry. The latter also makes it possible to analyze a sample in a multiparametric manner (several molecules analyzed in a single experiment, or even an entire proteome of interest) so as to be able to take an interest in systems without prejudging their properties.

This invention, by keeping the samples as close as possible to the cell culture, allows much more rapid analysis of recorded data: thousands of multiparametric experiments on a single chip. This is added to an interpretation, in phenotypic terms, that is much more evident and reliable. For example, no bias is introduced with regard to the quantification of the presence of a protein (no labeling, for example).

In addition, by directly integrating the mass spectrometry analysis on the chip or array containing the cells, the invention takes advantage of the high resolution of the device and allows high-throughput localized phenotype analyses (expression mapping and cell imaging).

These analyses are also quantitative, and therefore make it possible to study the modulation of expression over time.

This analytical quality applies to all the molecules present in the cell sample: secreted molecules, molecules present inside the cell (interfacing with a secretion device can also be envisioned), structural molecule.

Since the chemistry of the molecule only plays a role in terms of the practical implementation of the spectrometry, it is possible to detect any type of molecules produced by the cells: lipids, proteins, peptides, modified proteins, sugars, circulating RNAs.

The direct phenotyping of stimulated cells on a chip applies to all fields that involve the characterization of cell responses:
  Biological research: clinical and fundamental research on cells and intracellular or intercellular mechanisms of functioning are greatly accelerated by the use of a tool that directly employs cells and allows a high-throughput analysis coupled with high precision.
  Pharmaceutical research: by testing the activity of novel (therapeutic, toxic) molecules on living cells rapidly and in a multiparametric manner, the method of the invention makes it possible to accelerate the screening process, by carrying out tests that are close to in vivo conditions much earlier. In addition, the search for novel targets of therapeutic interest is also accelerated since their relevance is evaluated in a complete and relatively undisturbed cellular environment.
  Toxicology/biosensors: rapid analysis of the response of cells to toxins with respect to multiple parameters (several cell models on the same chip, for example) for, for example, the military industry or the environment industry.
Studies of genetic manipulations of plant or animal cells.

EXPERIMENTAL SECTION

Example 1

Analysis of T Lymphocyte Secretions Cytokine IL-2

Advantage: Characterization of samples from patients suffering from various viruses (hepatitis C, HIV, for example) or cancers. The cytokine analyzed (IL-2) is a promoter of T lymphocyte proliferation; it can be used as a therapy for strengthening the immune system. The measurement of the amount of cytokine is an indicator of the progression of the disease and/or of the therapy.

The principle of this experiment is to try to detect, by mass spectrometry, the secretion/production of cytokine IL-2 by stimulating T lymphocytes (DO10.11 line, property of INSERM U548). The stimulation can be carried out either directly (addition of the stimulating antigen to the solution) or by means of associated antigen-presenting B lymphocytes (themselves stimulated for presentation).

A drop of T lymphocyte cell culture (1500 cells in a drop of 4 µl of RPMI medium+10% FCS_fetal calf serum+1% PS) is deposited onto a MALDI-TOF spectrometry chip. As controls, drops containing antigen alone in solution, cytokine alone in solution, culture medium alone, or nonstimulated cells in culture, are deposited in the same manner. Cytokine production is subsequently stimulated in the drops in question.

The matrix (saturated solution of sinapinic acid or of alpha-cyano-4-hydroxycinnamic acid) is added to each spot and dried. The chip is placed in the spectrometer and the spectra are recorded and analyzed.

Several variants can be envisioned and combined:
  the matrix is deposited before the cells,
  functionalization of the surface using anti-cytokine antibodies, before the deposits are made, and the cells are possibly lyzed after stimulation,
  no matrix is deposited.

Example 2

Analysis of a Molecular Signature

The aim of this experiment is to demonstrate that it is possible to analyze a cell culture on a chip format, and more particularly to distinguish a molecular signature.

As a sample, we used a cell culture (jurkat line, concentration of $2 \times 10^6$ cell/ml in their culture medium RPMI+10% FCS–fetal calf serum), and also a sample of a recombinant protein (IL-2 available from R&D Systems under the reference 202-IL-050).

The chip used is part of the ProteinChip® system sold by the company Ciphergen Inc., using SELDI. It is a slide covered with a hydrophobic layer pierced with hydrophilic holes, where the active surface is made of silica, having the commercial reference NP20, which makes it possible to selectively retain proteins that are hydrophilic in nature. This chip contains 8 spots marked A to H.

The intention was to study the spectral signature of the protein without cells on a first chip. For this, a specific dilution of the protein, ranging from 5000 U/ml for spot A to 1 U/ml for spot H (encoding 2500, 1000, 500, 100, 50 and 10) was placed on each spot.

Preparation of the Matrix:
  The matrix sold by Ciphergen (commercial reference "EAM SPA"), sinapinic acid, is dissolved in 75 µl of acetonitrile and 75 µl of 1% TFA.
  The solution is vortexed for 5 min.
  The solution is centrifuged for 2 min at 10 000 rpm.

Calibration of the Device:
  A mixture of 1 µl of "All-in-one peptide mix" and 1 µl of matrix is deposited onto a spot of the chip.
  This is allowed to dry in ambient air.
  The calibration procedure of the ProteinChip® program is followed.

Preparation of the Chip:
  the slide is preincubated with distilled water (5 µl per spot for 1 min),
  the spots are dried using absorbent paper (without touching the surface),
  5 µl of sample are deposited per spot,
  this is left to dry in the open air,
  rinsing is carried out with distilled water (liquid is taken from the edge of the spot with a pipette, several times),
  the spots are allowed to dry, the matrix for promoting desorption/ionization (0.8 µl) is added, it is allowed to dry, the step consisting in adding desorption/ionization matrix followed by drying is repeated.

Reading the chip: use of the SELDI system of the CHU [University Hospital Teaching Center] in Grenoble (inserm U318).

| Settings: | Intensity: | 210 |
| --- | --- | --- |
| | High mass | 100 000 Da |
| | Deflector | auto (10 000 Da) |
| | Sensitivity | 10 |
| | Optimization range: | 10 000-20 000 Da |
| | Center mass: | 15 400 Da |

The spectra are determined using the ProteinChip® Software.

In a second step, a chip containing the samples of interest as explained in the table below is prepared:

The chip is incubated for 24 h so as to allow the cells to adhere.

The drops are subsequently irradiated selectively through an appropriate mask, that allows the UV radiation to pass only onto the spots supposed to receive it, with several irradiation times (by changing the masks during the experiment) and/or several intensities (mask more or less opaque).

After stimulation, the cells are left in culture for several incubation times (one chip per incubation time), for example, 0, 1 h, 4 h, 24 h and 48 h, so as to analyze the change in phenotype.

The samples are then frozen, matrix is added thereto (sinapinic acid, for example) and they are dried and then introduced into the mass spectrometer so as to be analyzed therein.

A mean of 50 spectra (equivalent to 50 laser bursts) per point (or pixel) is recorded, one point having a resolution of the size of the laser beam (less than 25 µm in diameter). For each point, the spectrum gives us a set of peaks. A suitable program makes it possible to select a peak of interest, and an image of the distribution of the compound described by this peak over the entire sample is retranscribed.

The mass of the compounds of interest allows us to refer back to its nature (by consulting databases), or else, if it is an unknown compound, the experiment can be repeated while adding more complete analysis thereto (for example, by following the first spectra with a multidimensional MS analysis).

| Spot | Sample |
| --- | --- |
| A | Calibration (1 µl "All-in-one peptide mix" + matrix) |
| B | 5 µl of culture medium without cells (RPMI = 10% FCS) |
| C | 5 µl of IL2 at . . . U/ml in culture medium |
| D | 5 µl of cells in their culture medium (concentration . . . cell/ml) |
| E | 5 µl of cells in their culture medium (concentration . . . cell/ml) (duplicate of D) |
| F | Idem D + 1 µl of IL2 at . . . U/ml |
| G | Duplicate of F |
| H | |

The samples (B to G) are deposited onto the chip according to the above protocol.

Example 3

Imaging of Part of the Proteom of Cells (3T3 Fibroblast) after UV-Irradiation

Objectives: In order to very rapidly determine the effects of a drug on the response of skin cells to UV-irradiation, and to aid with the targeting of these drugs to a specific cellular compartment, it is advantageous to study the distribution of some of the proteins expressed by these cells.

Implementation:

Cells (3T3 fibroblast) are cultured in a drop on a stainless steel MALDI target (for example, available from Brüker Daltonics Inc.). Drops of culture media without cells are deposited onto the chip in the same manner, as controls. The chip is placed in a controlled-atmosphere and controlled-temperature chamber (37° C., 100%, $H_2O$, 5% $CO_2$).

Several Chips are Thus Fabricated.

Example 4

Imaging of the Distribution of Calcium Ions in Cell Cultures by TOF-SIMS and Laser SNMS Advantage: calcium ions tend to accumulate in damaged cells.

Implementation:

The cells are cultured on a silicon chip, and are subjected or not subjected to one or more mechanical stresses, and the samples are then treated cryogenically.

They are subsequently introduced into the spectrometer under vacuum (beam of ions of 50 to 200 nm in diameter) and scanned with the beam under the same conditions as in Example 3.

The results are developed according to the same steps as in the previous example.

Example 5

Demonstration of a Spectral Profile Corresponding to a Specific Phenotype

The aim of this experiment is to illustrate the discrimination between several phenotypes by mass spectrometry on cell culture drops. We studied cytotoxicity phenomena with the use of CDDP (cisplatin=CIS-DIAMINEDICHLORO-PLATINUM, property of INSERM unit 318), which is an anticancer drug used in chemotherapy; and also apoptosis (programmed cell death) with the use of TNF (tumor necrosis factor).

The chips used are part of the ProteinChip® system sold by the company Ciphergen Inc. (see Example 2), using the SELDI system. The chip is more particularly the NP20 chip (commercial reference: C553-0043 NP20 ProteinChip Array, A-H Format), the hydrophilic surface of which is made of silica.

We used the U373 cell line (available from the supplier ECACC under the number 89081403).

All the steps that follow were carried out under sterile conditions.

Initially, the NP20 chips were immersed in 70% alcohol for 20 min and dried at ambient temperature under a hood. The cell cultures (in DMEM culture medium+10% fetal calf serum) were deposited, in 5 µl drops, onto 2 chips as indicated in the table below:

| Spot | Cells | Cytotoxicity treatments (chip No. 1) | Apoptosis treatments (chip No. 2) |
|---|---|---|---|
| A | Culture medium without cells | With CDDP (1 µl: final concentration $5 \times 10^{-6}$) | With TNF |
| B | 20 000 cells | | |
| C | 20 000 cells | | |
| D | 20 000 cells | | |
| E | Culture medium without cells | | |
| F | 20 000 cells | Without CDDP | Without TNF |
| G | 20 000 cells | | |
| H | 20 000 cells | | |

The chips were subsequently allowed to incubate in an incubator in an atmosphere saturated with water at 37° C. under 5% $CO_2$ for one day.

Then, in accordance with the conditions disclosed in the table, 1 µl of CDDP diluted in cell culture medium was deposited into drops A, B, C and D of chip No. 1, so as to achieve a final concentration of approximately $5 \times 10^{-6}$ M. On chip No. 2, 0.2 µl of TNF was deposited into drops A, B, C and D so as to obtain a final concentration of approximately 0.01 µg/ml.

The devices were then left to incubate as above in the incubator for 1 day.

The manipulations that follow were carried out under non-sterile conditions.

Before introduction of the chips into the mass spectrometer, they were soaked in a 2 mM Hepes solution. They were allowed to dry at ambient temperature (10-15 min).

A matrix solution (sinapinic acid) was prepared beforehand according to the protocols recommended by Ciphergen Inc.: the matrix was dissolved in 75 µl of acetonitrile and 75 µl of a 1% aqueous trifluoroacetic acid solution. The solution was subsequently mixed for 15 min on a vortex, and then centrifuged (10 000 rpm) for 2 min just before it was used.

2 times 0.8 µl of matrix was added to each spot, allowing time to dry between each deposit (3-5 min).

Reading of Chips:

The chips were then analyzed in the Ciphergen SELDI-TOF mass spectrometer.

The intention was to analyze the entire mass range accessible to the spectrometer. Three analyses were therefore carried out on each chip for 3 mass ranges (low, medium and high). The spectra are produced using the ProteinChip® Software from Ciphergen Inc.

The settings were effected as explained in the table below:

| Passage | Low | Medium | High |
|---|---|---|---|
| Laser intensity | 178 | 198 | 230 |
| High masses (in Da) | 100 000 | 200 000 | 300 000 |
| Deflector (in Da) | 1500 | 3000 | 5000 |
| Sensitivity | 10 | 10 | 10 |
| Optimization low masses (in Da) | 2000 | 5000 | 20 000 |
| Optimization high masses (in Da) | 20 000 | 50 000 | 150 000 |

Laser shots were fired on positions 21 to 81 for the "low" passages, in steps of 5, with 2 heating bursts (intensity+5) per position. They were not included in the mean of the 15 shots per position that, when added, form the final spectra. The medium passages use positions 22 to 82 and the "high" passages use positions 23 to 83.

The results of the assays are given in FIGS. 11, 12 and 13.

FIG. 11: Example of a spectrum obtained without CDDP and without TNF. Along the x-axis is the mass to charge ratio in Daltons (Da); along the y-axis is the signal intensity (100 corresponds to saturation of the detector).

FIG. 12: Representation of the differences between the spectra of the two phenotypes without TNF and with TNF.

FIG. 12 shows the differences in intensity between two phenotypes for each peak of the spectra on a logarithmic scale: in blue, the profile of cells stimulated with TNF (and therefore in apoptosis); in red, the profile of nonstimulated cells. FIG. 13 shows, in the same way, in blue, the profile of the cells stimulated with TNF; in red, that of the cells stimulated with CDDP; and, in green, that of the nonstimulated cells.

FIG. 13: Representation of the differences between the spectra of the 3 phenotypes without either TNF or CDDP, with TNF and with CDDP.

These results demonstrate that it is possible not only to differentiate between nonstimulated cells and stimulated cells, but also to differentiate between 2 significantly different phenotypes.

In addition, these phenotypes could not have been studied in a conventional manner before several days of incubation, the labeling being carried out after 3 days for the cytotoxicity and after 6 days for the apoptosis.

The spectra obtained (see, for example, FIG. 11) were subsequently analyzed in order to verify that characteristic phenotype signatures were obtained.

The invention claimed is:

1. A method for analyzing at least one reaction medium comprising at least one cell C, comprising:
   (i) depositing at least one reaction medium containing the cell C onto a support S comprising a substantially planar surface and contained within a controlled atmosphere chamber, in the form of aqueous drops comprising the cell C and a solution of culture medium on said surface;
   (ii) covering the substantially planar surface of the support S onto which the aqueous drops containing the cell C has have been deposited with a separating film F that allows gases to pass through and prevents evaporation of the aqueous drops deposited onto the support S;
   (iii) growing the cell on the planer surface of the support S;
   (iv) optionally applying to the aqueous drops containing the cell C one or more treatment steps;
   (v) preparing and introducing the support S contained within the controlled atmosphere chamber and supporting the reaction medium into a mass spectrometer;
   (vi) desorbing and ionizing the reaction medium in the mass spectrometer; and
   (vii) recording and analyzing the mass spectrum of the reaction medium.

2. The method as claimed in claim 1, wherein, before step (iv), the cell C is subjected to a stimulation.

3. The method as claimed in claim 2, wherein the stimulation to which the cell C is subjected is selected from the group consisting of:
   the introduction of a reagent R;
   being brought into contact with one or more cells;
   a supply of energy;

the application of an electric field or of a magnetic field; and an optical treatment.

4. The method as claimed in claim 3, wherein the reagent R is selected from the group consisting of inorganic molecules, natural organic molecules, molecules derived from organic synthesis or from combinatorial synthesis, molecules extracted from biological samples, and molecules extracted from biological samples, which have been modified by synthesis.

5. The method as claimed in claim 4, wherein the molecules are selected from the group consisting of single-stranded and double-stranded DNAs, single-stranded and double-stranded RNAs, and proteins and peptides.

6. The method as claimed in claim 1, wherein the attachment of the drops to the support S occurs due to surface tension forces.

7. The method as claimed in claim 1, wherein the depositing of the aqueous drops containing a cell onto the support S, and optionally under the separating film F, is carried out by means of fine capillaries.

8. The method as claimed in claim 1, wherein the depositing of the aqueous drops containing a cell onto the support S is carried out by means of a piezoelectric system.

9. The method as claimed in claim 1, wherein the one or more treatment steps selected from the group consisting of cell lysis, one or more washes, and the adsorption or the attachment of molecules.

10. The method as claimed in claim 1, further comprising in step (iv) at least one step consisting of treating the reaction medium or media placed on the support S with a solution of molecules that promote desorption.

11. The method as claimed in claim 1, wherein the preparing in step (v), with a view to introduction into the mass spectrometer, comprises at least one step selected from the group consisting of freezing the reaction medium; drying the reaction medium with or without heat treatment and with or without a vacuum; and fixing the reaction medium by means of a treatment with an agent.

12. The method as claimed in claim 11, wherein the agent comprises methanol or formaldehyde.

13. The method as claimed in claim 1, wherein the preparing in step (v), with a view to introduction into the mass spectrometer, comprises the addition to the reaction medium of one or more acid molecules that are small in size and absorb light, followed by drying.

14. The method as claimed in claim 13, further comprising at least the following steps:
introduction of the reaction medium placed on the support S into a mass spectrometer tube;
application of a vacuum and of an electric field in the spectrometer tube;
application of a desorption/ionization treatment in a controlled and sequenced manner on the reaction medium; and
detection of the mass of the ions formed.

15. The method as claimed in claim 1, further comprising at least one step consisting of comparing the recorded mass spectrum with a mass spectrum bank.

16. A device for analyzing at least one reaction medium comprising at least one cell C, the device comprising the following:
a reaction medium containing cell C in a solution of culture medium,
a support S comprising a substantially planar surface, wherein the surface of the support S is covered with a separating film F that allows gases to pass through and prevents evaporation of the aqueous drops of the reaction medium deposited onto the support S; wherein the support S is used as samples support in a mass spectrometer;
a controlled-atmosphere chamber in which the support S is placed so as to allow the survival of the cell C;
means for depositing onto said surface aqueous drops of the reaction medium containing the cell C suspended in the culture medium;
means for desorbing and ionizing the reaction medium comprising the cell C while deposited on the surface of support S: and
a mass spectrometer.

17. The device as claimed in claim 16, wherein the controlled-atmosphere chamber is an incubator at a temperature ranging from 35 to 42° C., the $CO_2$ level is maintained at between 3 and 5%, and the oxygen $O_2$ level is that of ambient air.

18. The device as claimed in claim 17, wherein the temperature ranges from 36.5 and 37.5° C.

19. The device as claimed in claim 16, wherein the separating film F is selected from the group consisting of:
a non-water-miscible liquid;
a gas;
a flexible, solid film; and
a rigid honeycombed cover comprising cavities made of porous material, the size of the cavities being adjusted so as to be able to contain the drop of cell(s) and, optionally, a drop of reagent.

20. The device as claimed in claim 16, wherein the support S consists of a plate that is made of silicon, glass, or a polymer.

21. The device as claimed in claim 16, wherein the support S comprises an electrically conducting layer.

22. The device as claimed in claim 16, wherein the support S has a substantially planar surface comprising at least one means for receiving the aqueous drops.

23. The device as claimed in claim 22, wherein the means for receiving the aqueous drops consists of one of the following:
the support S exhibits a hydrophobic nature on its planar surface and comprises one or more hydrophilic areas;
the support S comprises cavities of a depth ranging from 1 micron to 1 millimeter on its planar surface;
the support S is a plate equipped with outgrowth of small thickness, from 1 micron to 1 millimeter, arranged on its surface and intended to promote the attachment of the drops; and
the support S is a plate equipped with at least one wire, onto which the drops attach.

24. The device as claimed in claim 16, wherein the support S is mobile.

25. The device as claimed in claim 16, wherein the means for depositing aqueous drops and for desorbing and ionizing the reaction medium are connected to a control device that allows the means to be automated.

26. The device as claimed in claim 16, wherein the support S comprises means for receiving the drops, arranged regularly in the form of a matrix.

27. The device as claimed in claim 26, further comprising at least one piece of equipment for measuring the mass of the reaction medium by means of mass spectrometry; the piece of equipment comprising a spectrometer tube, a device for creating a vacuum in the tube; electrical means for applying an electrical acceleration potential in the tube so as to accelerate the molecules of the reaction medium to be analyzed; a means for detecting the mass of the ions formed; a means of introducing the support S into the tube; and a means for the desorption and the ionization of the sample reaction medium to be treated.

28. The device as claimed in claim 27, wherein the means of detecting the mass is selected from the group consisting of:
    TOF: time of flight;
    MS/MS: tandem mass spectrometry or multidimensional mass spectrometry;
    Quadrupole (or ion trap); and
    FT-MS or FT-ICR: Fourier-Transform mass spectrometry-ion cyclotron resonance.

29. The device as claimed in claim 16, wherein the desorption means is selected from the group consisting of a laser beam; a beam of ions; a beam of neutral atoms; a beam of electrons; and the spraying of a liquid sample.

30. The device as claimed in claim 16, wherein the desorption/ionization means is selected from the group consisting of:
    MALDI: matrix assisted laser desorption ionization;
    SELDI: surface enhanced laser desorption ionization;
    SIMS: secondary ion mass spectrometry;
    SLAMS: secondary neutral mass spectrometry;
    ESI: electrospray ionization;
    FAB: fast atom bombardment; and
    APCI: atmospheric pressure chemical ionization.

31. A method for analyzing at least one reaction medium Comprising at least one cell C comprising;
    (i) depositing within a controlled atmosphere chamber aqueous drops containing live cell C and a culture medium onto a support S having a substantially planar surface,
    (ii) covering the substantially planar surface of the support S onto which the aqueous drops containing the cell C has been deposited with a separating film F that allows gases to pass through and prevents evaporation of the aqueous drops deposited onto the support S;
    (iii) growing said live cell C on the substantially planar surface of support S,
    (iv) optionally stimulating said live cell C,
    (v) contacting said cell C on the substantially planar surface with at least one Reagent,
    (vi) preparing said cell C on the substantially planar surface of support S after Contact with said at least one reagent for mass spectrometry,
    (vii) introducing said preparation into a mass spectrometer;
    (viii) desorbing and ionizing the preparation in the mass spectrometer; and
    (ix) recording and analyzing the mass spectrum of the preparation.

* * * * *